United States Patent
Wang et al.

(10) Patent No.: US 9,510,792 B2
(45) Date of Patent: Dec. 6, 2016

(54) APPARATUS AND METHOD FOR COLLIMATING X-RAYS IN SPECTRAL COMPUTER TOMOGRAPHY IMAGING

(71) Applicant: TOSHIBA MEDICAL SYSTEMS CORPORATION, Otawara-Shi (JP)

(72) Inventors: Xiaolan Wang, Buffalo Grove, IL (US); Yuexing Zhang, Naperville, IL (US); Yu Zou, Naperville, IL (US); Miesher L. Rodrigues, Buffalo Grove, IL (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 207 days.

(21) Appl. No.: 13/896,949

(22) Filed: May 17, 2013

(65) Prior Publication Data

US 2014/0341333 A1    Nov. 20, 2014

(51) Int. Cl.
*H01L 27/146* (2006.01)
*H01L 27/148* (2006.01)
(Continued)

(52) U.S. Cl.
CPC ............. *A61B 6/032* (2013.01); *A61B 6/06* (2013.01); *A61B 6/4241* (2013.01);
(Continued)

(58) Field of Classification Search
CPC .......... G21K 1/00; G21K 1/02; G21K 1/025; G21K 1/04; G21K 1/10; A61B 6/06; A61B 6/00; A61B 6/02; A61B 6/03; A61B 6/032; A61B 6/035; A61B 6/42; A61B 6/4208; A61B 6/4233; A61B 6/4241; A61B 6/4266; A61B 6/4291; A61B 6/44; G01T 1/16; G01T 1/24; G01T 1/241; G01T 1/2018; G01T 1/00; G01T 1/243; G01T 1/244; H01L 27/146; H01L 27/14601; H01L 27/14625; H01L 27/1463; H01L 27/14634; H01L 27/148; H01L 27/14806; H01L 27/14818; H01L 25/00; H01L 25/03; H01L 25/10; H01L 25/105; H01L 31/00; H01L 31/02; H01L 31/0203; H01L 31/0224; H01L 31/0232; H01L 31/02327; H01L 27/00; H01L 27/04; H01L 27/10; H01L 27/14; H01L 27/142; H01L 27/144; H01L 27/1446; H01L 27/14603; H01L 27/14607; H01L 27/14618; H01L 27/14643; H01L 27/14658; H01L 27/14659; G01B 11/02; G01B 11/026; G01B 11/14; G01B 11/26; G01B 11/27; G01B 11/272; G02B 5/00; G02B 5/003; G02B 27/09; G02B 27/30
USPC ........... 378/4, 8, 19, 20, 145, 147, 149–154, 378/189, 204, 210; 250/370.01, 370.06, 250/370.08, 370.09, 370.1, 370.12, 370.13, 250/370.14, 371; 356/138, 139.04, 139.05, 356/139.07, 625, 634–636; 359/227, 298, 359/601, 614, 641
See application file for complete search history.

(56) References Cited

U.S. PATENT DOCUMENTS 4,638,499 A * 1/1987 Eberhard et al. .................. 378/7
4,856,041 A * 8/1989 Klein et al. ..................... 378/147
(Continued)

FOREIGN PATENT DOCUMENTS

JP    2013-40859 A    2/2013

*Primary Examiner* — Anastasia Midkiff
(74) *Attorney, Agent, or Firm* — Oblon, McClelland, Maier & Neustadt, L.L.P.

(57) ABSTRACT

A detector includes a photon-counting detector (PCD) layer and a cathode layer arranged adjacent to the PCD layer. The detector further includes a plurality of pixilated anodes arranged adjacent to the photon-counting detecting layer on a side opposite to the cathode layer. The detector also includes a plurality of collimator segments arranged above the cathode layer so as to block a portion of X-ray photons emitted from an X-ray source from reaching the anodes, where each collimator segment is arranged above a portion of at least one anode.

21 Claims, 19 Drawing Sheets

(51) Int. Cl.
*A61B 6/06* (2006.01)
*G21K 1/02* (2006.01)
*G06T 1/00* (2006.01)
*A61B 6/03* (2006.01)
*G01T 1/24* (2006.01)
*H01L 25/03* (2006.01)
*A61B 6/00* (2006.01)

(52) U.S. Cl.
CPC ............ *A61B 6/4291* (2013.01); *G01T 1/241* (2013.01); *G21K 1/025* (2013.01); *H01L 27/1463* (2013.01); *H01L 27/14603* (2013.01); *H01L 27/14607* (2013.01); *H01L 27/14625* (2013.01); *H01L 27/14658* (2013.01); *H01L 27/14806* (2013.01); *H01L 27/14818* (2013.01); *A61B 6/035* (2013.01); *A61B 6/4233* (2013.01); *A61B 6/4266* (2013.01); *A61B 6/4275* (2013.01); *A61B 6/44* (2013.01); *A61B 6/482* (2013.01); *G01T 1/244* (2013.01); *G01T 1/249* (2013.01); *G21K 1/02* (2013.01); *H01L 25/03* (2013.01); *H01L 27/146* (2013.01); *H01L 27/148* (2013.01); *H01L 27/14601* (2013.01); *H01L 27/14618* (2013.01)

(56) References Cited

U.S. PATENT DOCUMENTS

| | | | |
|---|---|---|---|
| 4,866,744 A * | 9/1989 | Yoshida | 378/7 |
| 6,175,615 B1 * | 1/2001 | Guru | G21K 1/025 378/147 |
| 6,681,866 B1 * | 1/2004 | Raducha et al. | 172/452 |
| 6,696,686 B1 * | 2/2004 | Wainer et al. | 250/363.1 |
| 7,339,176 B2 * | 3/2008 | El-Hanany et al. | 250/370.09 |
| 7,564,940 B2 * | 7/2009 | Mattson et al. | 378/19 |
| 7,592,597 B2 * | 9/2009 | Hefetz et al. | 250/363.1 |
| 2003/0128801 A1 * | 7/2003 | Eisenberg et al. | 378/19 |
| 2005/0089145 A1 * | 4/2005 | Ross et al. | 378/147 |
| 2006/0023832 A1 * | 2/2006 | Edic | A61B 6/032 378/7 |
| 2008/0175347 A1 * | 7/2008 | Tkaczyk | G01T 1/24 378/7 |
| 2008/0247504 A1 * | 10/2008 | Edic | A61B 6/032 378/9 |
| 2009/0039273 A1 * | 2/2009 | Tkaczyk | G01T 1/171 250/370.06 |
| 2009/0052612 A1 * | 2/2009 | Wu | A61B 6/032 378/5 |
| 2009/0080597 A1 * | 3/2009 | Basu | A61B 5/4869 378/5 |
| 2009/0080601 A1 * | 3/2009 | Tkaczyk | G01T 1/24 378/19 |
| 2010/0038548 A1 * | 2/2010 | Guerin et al. | 250/370.09 |
| 2011/0156198 A1 * | 6/2011 | Chen et al. | 257/448 |
| 2011/0211667 A1 * | 9/2011 | Ikhlef | A61B 6/032 378/19 |
| 2011/0222648 A1 * | 9/2011 | Tischenko et al. | 378/14 |
| 2012/0108948 A1 * | 5/2012 | Jansen | A61B 6/037 600/411 |
| 2012/0189094 A1 * | 7/2012 | Neushul et al. | 378/19 |
| 2012/0257710 A1 * | 10/2012 | Funk | 378/9 |
| 2012/0305781 A1 * | 12/2012 | Jansen | G02B 27/30 250/363.04 |
| 2013/0329856 A1 * | 12/2013 | Kuwahara | A61N 5/1039 378/62 |

* cited by examiner

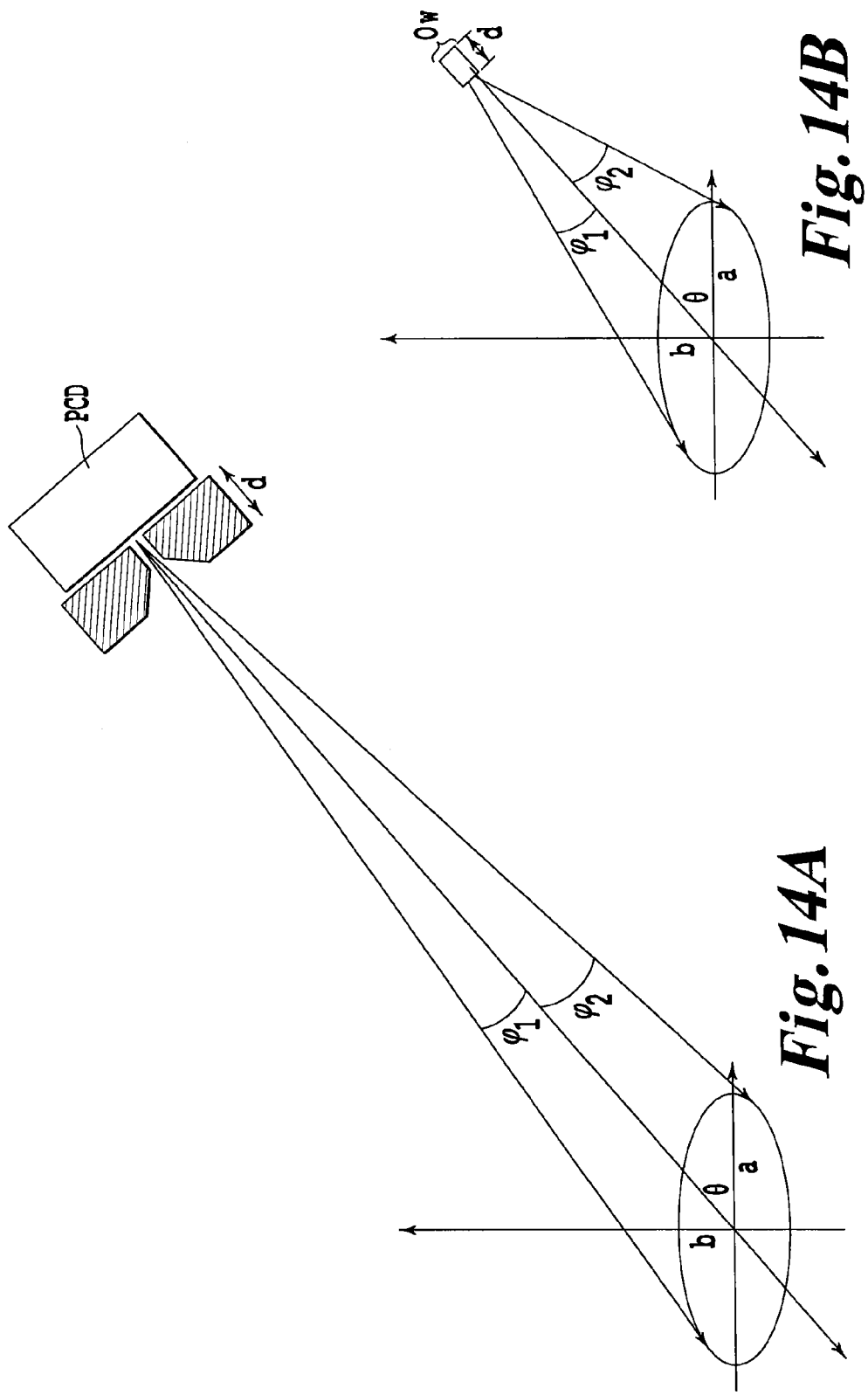

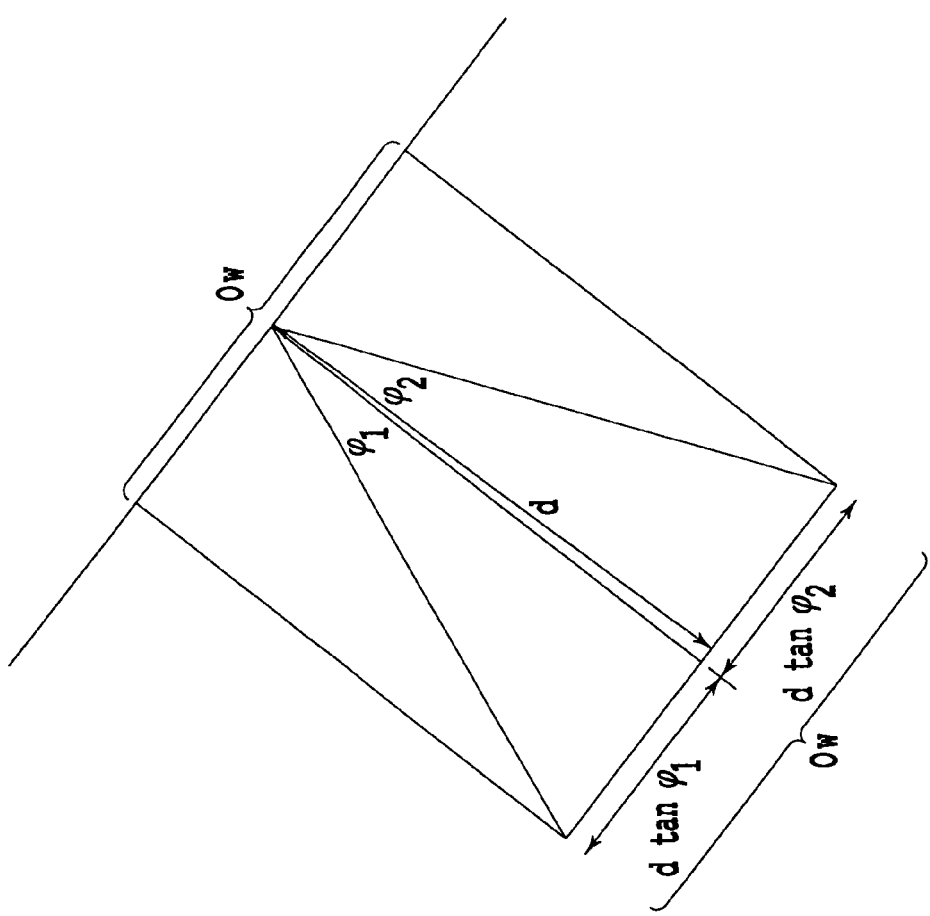

APPARATUS AND METHOD FOR COLLIMATING X-RAYS IN SPECTRAL COMPUTER TOMOGRAPHY IMAGING

FIELD

Embodiments disclosed herein generally relate to Computed Tomography (CT). In particular, embodiments disclosed herein relate to an apparatus and method for collimating X-rays incident on photon-counting detectors (PCDs) in spectral CT imaging.

BACKGROUND

X-ray tomographic imaging, in its simplest expression, is an X-ray beam traversing an object, and a detector relating the overall attenuation per ray. The attenuation is derived from a comparison of the same ray with and without the presence of the object. From this conceptual definition, several steps are required to properly construct an image. For instance, the finite size of the X-ray generator, the nature and shape of the filter blocking the very low-energy X-rays from the generator, the details of the geometry and characteristics of the detector, and the capacity of the acquisition system are all elements that affect how reconstruction is performed.

Conventional X-ray detectors integrate the total electrical current produced in a radiation sensor, and disregard the amplitude information from individual photon detection events. Since the charge amplitude from each event is proportional to the photon's detected energy, this acquisition provides no information about the energy of individual photons, and is thus unable to capture the energy dependence of the attenuation coefficient in the object.

On the other hand, semiconductor X-ray detectors that are capable of single photon counting and individual pulse-height analysis may be used. These X-ray detectors are made possible by the availability of fast semiconductor radiation sensor materials with room temperature operation and good energy resolution, combined with application-specific integrated circuits (ASICs) suitable for multi-pixel parallel readout and fast counting.

One major advantage of such photon-counting detectors is that, when combined with pulse-height analysis readout, spectral information can be obtained about the attenuation coefficient in the object. A conventional CT measures the attenuation at one average energy only, while in reality, the attenuation coefficient strongly depends on the photon energy. In contrast, with pulse-height analysis, a system is able to categorize the incident X-ray photons into several energy bins based on their detected energy. This spectral information can effectively improve material discrimination and target contrast, all of which can be traded for a dose reduction to a patient.

Many clinical applications benefit from spectral CT capabilities such as material decomposition and beam hardening direction. One of the technical difficulties with a photon-counting detector system for general purpose CT is the limited count rate ability of the detector. Furthermore, semiconductor-based detectors have the problem of inter-pixel crosstalk. High X-ray flux, commonly encountered in CT scans, causes CdTe/CdZnTe-based photon-counting detectors to polarize and stop functioning. Thus, it is very important to achieve desirable detector responses under high flux. Furthermore, scattering correction is a very big technical challenge for multi-slice sparse fourth generation PCCT geometry.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 14A to 14C illustrate the geometric parameters for determining the opening of the wedge shaped collimators;

DETAILED DESCRIPTION

Figure 1:
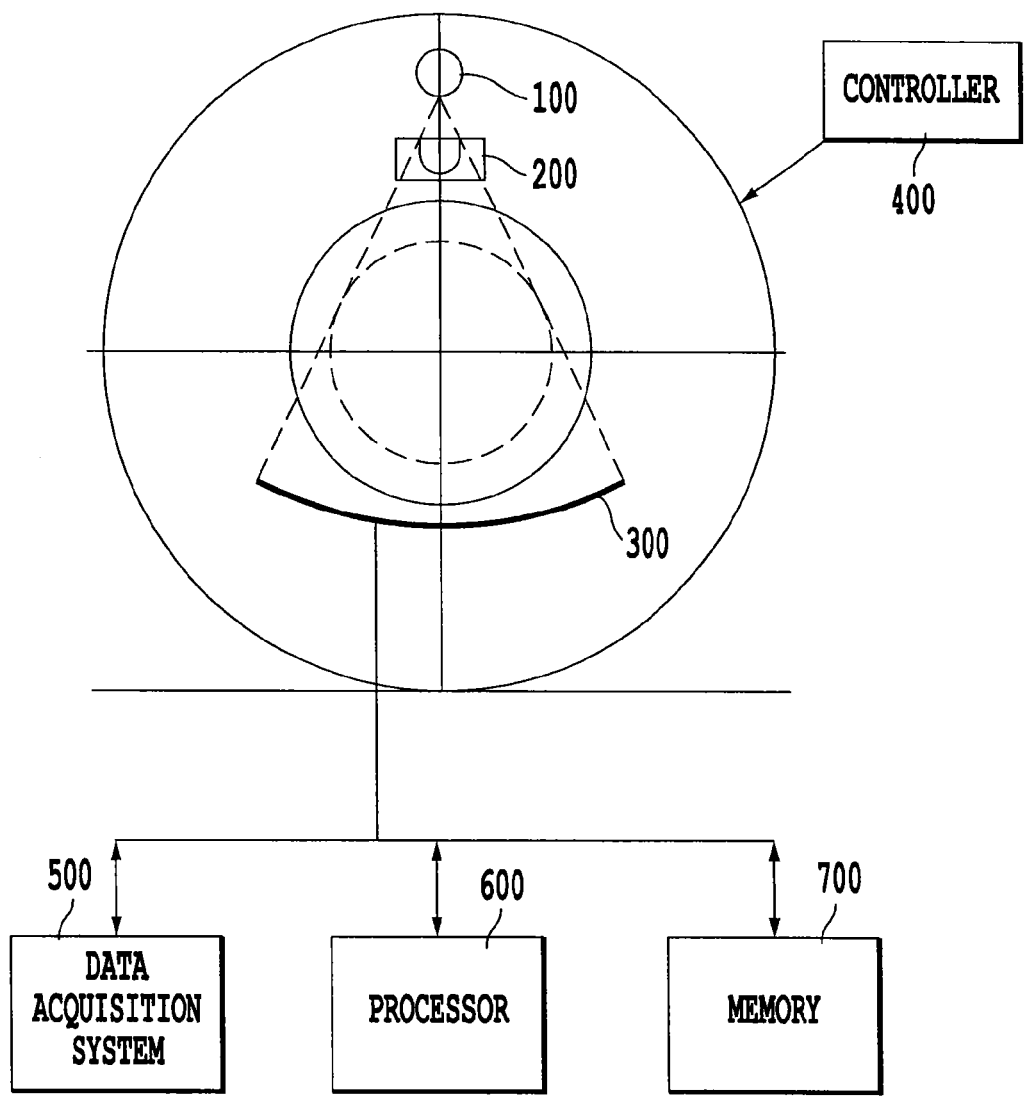
FIG. 1 illustrates a CT system.

Embodiments disclosed herein reduce the size of a beam onto a CZT detector channel by an aperture or slit for dramatically improved detector response under high flux. Using a collimator to block out X-rays incident on a PCD, where only a part of each channel is illuminated, reduces the electric field distortion and therefore, improves the performance of CT scanners. Furthermore, using a collimator also reduces inter-pixel crosstalk and the resulting spectral distortion.

Embodiments disclosed herein are directed to a focusing collimator between segments for a sparse fourth-generation CT scanner to reject the longitudinally scattered beam and help collimate the primary beam for the entire range of detector fan angle.

Embodiments disclosed herein are directed to "wedge shaped" collimators in the XY-plane (detector fan) direction to help compensate X-ray intensity variation and facilitate angular response correction. The "wedge shaped collimators" can have an adjustable mechanism.

Embodiments of the collimators disclosed herein use medium-Z materials (e.g., Mo) to minimize undesirable secondary events (e.g., scattering, escape X-rays) caused by the collimator.

According to one embodiment, a detector includes a photon-counting detector (PCD) layer and a cathode layer arranged adjacent to the PCD layer. The detector further includes a plurality of pixilated anodes arranged adjacent to the photon-counting detecting layer on a side opposite to the cathode layer. The detector also includes a plurality of collimator segments arranged above the cathode layer so as to block a portion of X-ray photons emitted from an X-ray source from reaching the anodes, where each collimator segment is arranged above a portion of at least one anode.

According to one embodiment, a computed-tomography (CT) apparatus includes a CT scanner including a rotating X-ray source. The apparatus further includes a photon-counting detector (PCD) array including a plurality of PCDs, where each PCD is configured to capture incident X-ray photons emitted from the X-ray source. The apparatus further includes a collimator having a curved surface extending away from an edge of one of the PCDs in the PCD array to block a portion of X-ray photons emitted from the X-ray source.

According to one embodiment, a computed-tomography (CT) apparatus includes a CT scanner including a rotating X-ray source. The apparatus further includes a plurality of photon-counting detectors (PCDs) arranged in a fixed detector ring around the X-ray source to capture incident X-ray photons emitted from the X-ray source. The apparatus also includes a pair of adjustable wedge-shaped collimators arranged on a surface of one of the PCDs to block X-ray photons emitted from the X-ray source.

According to one embodiment, a method to determine an opening distance of a pair of adjustable wedge-shaped collimators positioned on a photon-counting detector (PCD), includes performing a scanogram of an imaging subject centered with respect to a rotating X-ray source. The method further includes determining, using information from the scanogram, a pair of axis lengths of a pair of perpendicular axises that pass through a center of the imaging subject. The method further includes determining an angle between a line from the PCD to the center of the imaging subject and one of the axises from the pair of perpendicular axises. The method further includes determining the opening distance of the pair of adjustable wedge-shaped collimators using at least the determined pair of axis lengths and the determined angle. The method also includes adjusting an opening between the pair of adjustable wedge-shaped collimators in accordance with the determined opening distance.

According to one embodiment, a computed-tomography (CT) apparatus includes a CT scanner including a rotating X-ray source. The apparatus further includes a photon-counting detector (PCD) array including a plurality of PCDs, where each PCD is configured to capture incident X-ray photons emitted from the X-ray source. The apparatus also includes a collimator having a flat surface extending away from an edge of one of the PCDs in the PCD array to lock a portion of X-ray photons emitted from the X-ray source.

Referring now to the drawings, wherein like reference numerals designate identical or corresponding parts throughout the several views, FIG. 1 illustrates an embodiment of a structure of a CT apparatus that can include the detectors described herein. The CT apparatus of FIG. 1 includes an X-ray tube 100, filters and collimators 200, and detector 300. The CT apparatus will also include additional mechanical and electrical components such as a gantry motor and a controller 400 to control the rotation of the gantry, control the X-ray source, and control a patient bed. The CT apparatus also includes a data acquisition system 500 and a (reconstruction) processor 600 to generate CT images based on the projection data acquired by the data acquisition system. The processor and data acquisition system make use of a memory 700, which is configured to store e.g., data obtained from the detector and reconstructed images.

Figure 2:
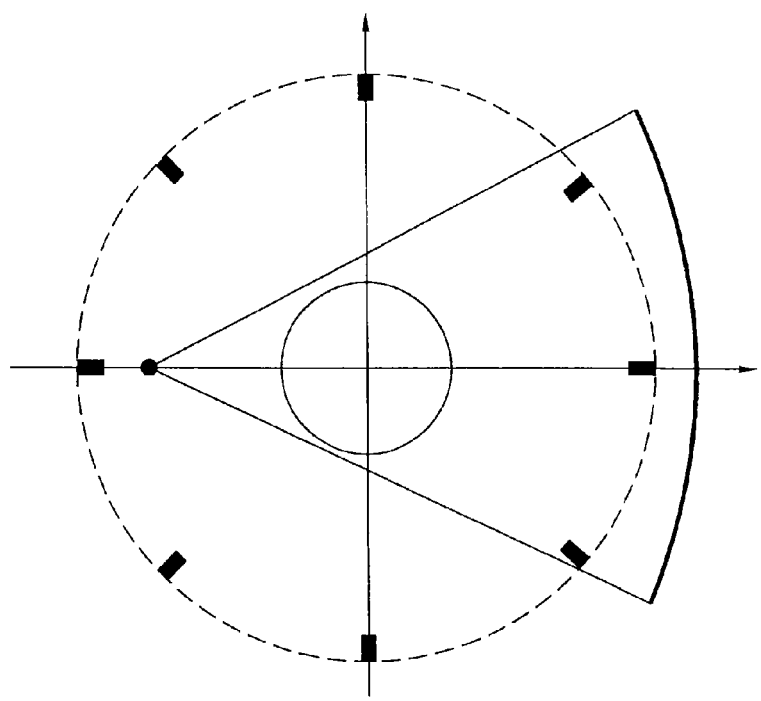
FIG. 2 illustrates a sparse CT scanner.

FIG. 2 illustrates a sparse spectral CT imaging system that includes stationary, sparse PCDs and a rotating X-ray source. The source trajectory may be inside or outside the ring defined by the photon-counting detectors.

Figure 3:
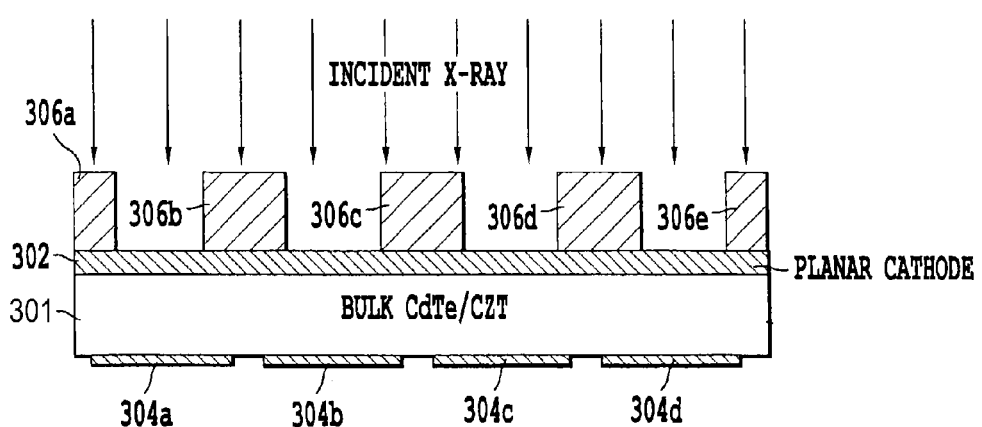
FIG. 3 illustrates an exemplary embodiment of a PCD with collimators.

FIG. 3 illustrates one embodiment of a PCD with collimators. As illustrated in FIG. 3, the PCD includes pixellated anodes 304a to 304d and planar cathode 302. In one embodiment, each of pixellated anodes 304a to 304d correspond to individual pixels. In some embodiments, the PCD is a semiconductor PCD having a detector layer 301 made of a continuous bulk material such as CdTe/CZT. As illustrated in FIG. 3, collimators 306a to 306e are positioned on the cathode side of the detector layer 301. In some embodiments the collimators 306a to 306e are provided on the edges of each pixel. In this regard, the collimators block out incident X-rays from hitting the edges of the pixels so that only the center of the pixels 304a to 304d receive the incident X-rays. Accordingly, as illustrated in FIG. 3, the installed collimators separate individual detector channels/pixels. In one embodiment, each of the collimators 306a-306e are part of a mask that is overlaid on the cathode side of the PCD. In another embodiment, 10%-60% of each of the anodes is covered by the collimators depending on the amount of flux incident on the PCD.

Figure 4:
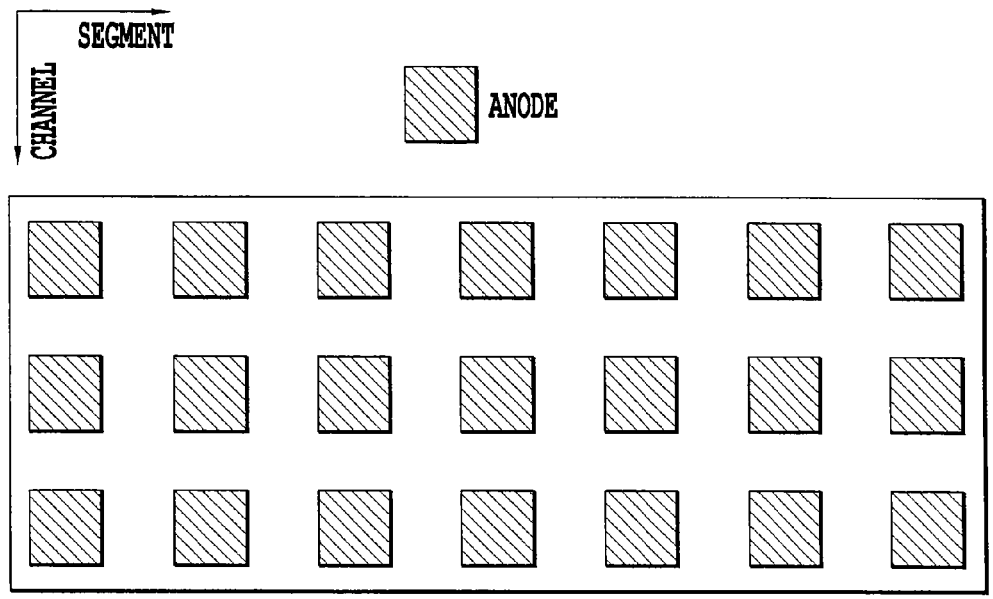
FIG. 4 illustrates a top view of the PCD having an anode pattern.

FIG. 4 illustrates a two-dimensional anode pattern on the bottom of a detector according to one embodiment. In some embodiments, the anodes represent individual pixel positions. According to one embodiment, the collimators are placed on the top (cathode size) of the detector. However, for illustration purposes, the figures illustrate an overlay of a collimator pattern including collimator segments on the anode pattern. In some embodiments, for a two-dimensional planar detector, a specific collimator pattern is determined for a specific detector geometry and imaging tasks. The upper left hand corner of FIG. 4 illustrates the segment and channel directions of the anode pattern.

Figure 5:
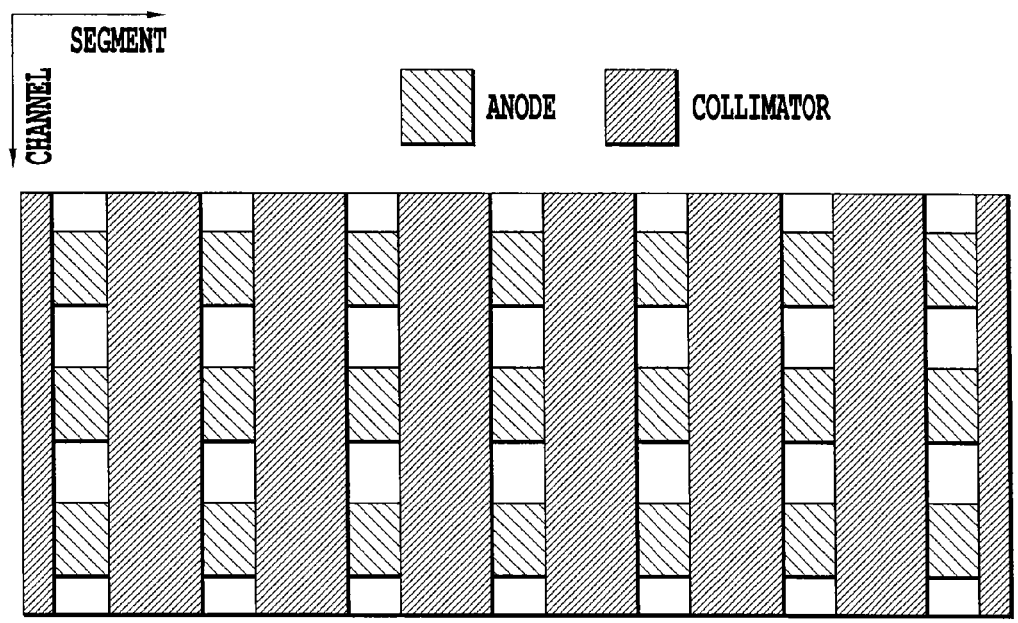
FIGS. 5-8 illustrate exemplary embodiments of collimator patterns with respect to the top view of the PCD detector having the anode pattern.

FIG. 5 illustrates an embodiment of a collimator pattern that is used when cross-talk in the segment direction (i.e, inter-segment cross talk) is a major concern. As illustrated in FIG. 5, the collimator pattern is configured to block out incident X-rays on the edges of each of the pixels (anodes) in the segment direction. That is, the collimator pattern includes collimator segments between each column of pixels in the segment direction.

Figure 6:
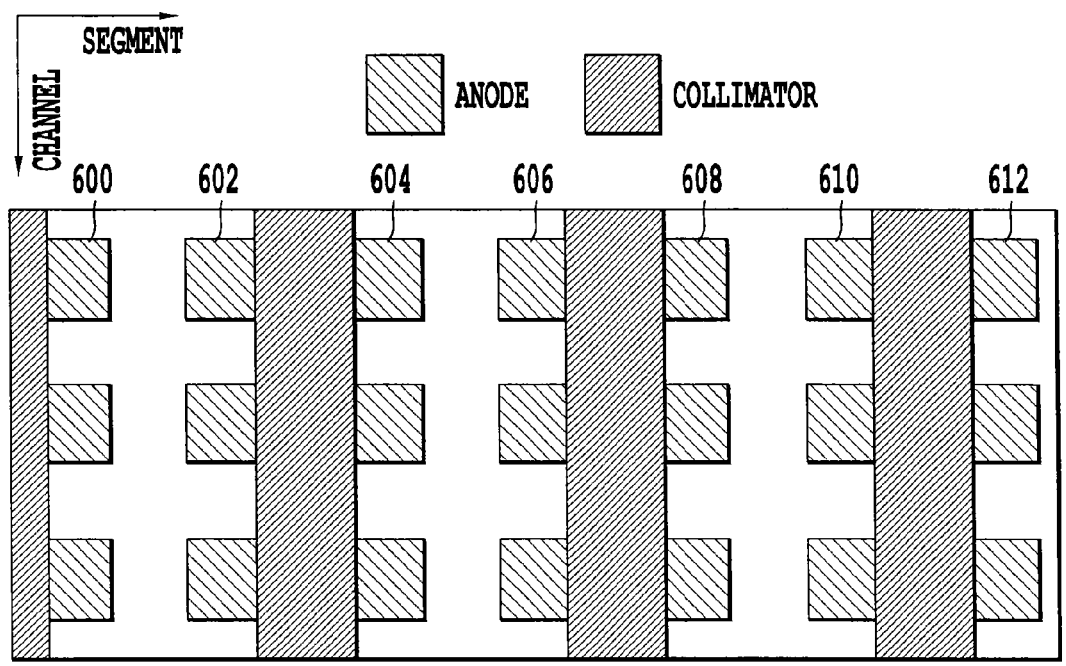

FIG. 6 illustrates another embodiment of a collimator pattern for a PCD array. In this particular configuration, collimator segments are positioned between every other pair of adjacent pixels. The collimator pattern illustrated in FIG. 6 is used when signals from every two pixels in the segment direction are combined. Therefore, isolation is needed for every other segment. For example, in FIG. 6, pixel 600 is combined with pixel 602, pixel 604 is combined with pixel 606, and pixel 608 is combined with pixel 610. Therefore, the collimator pattern includes collimator segments between pixels 602 and 604, between 606 and 608, and between 610 and 612. In this scenario, to achieve a better signal-to-noise ratio (SNR), signals from multiple detector pixels are combined to provide better counting statistics.

Figure 7:
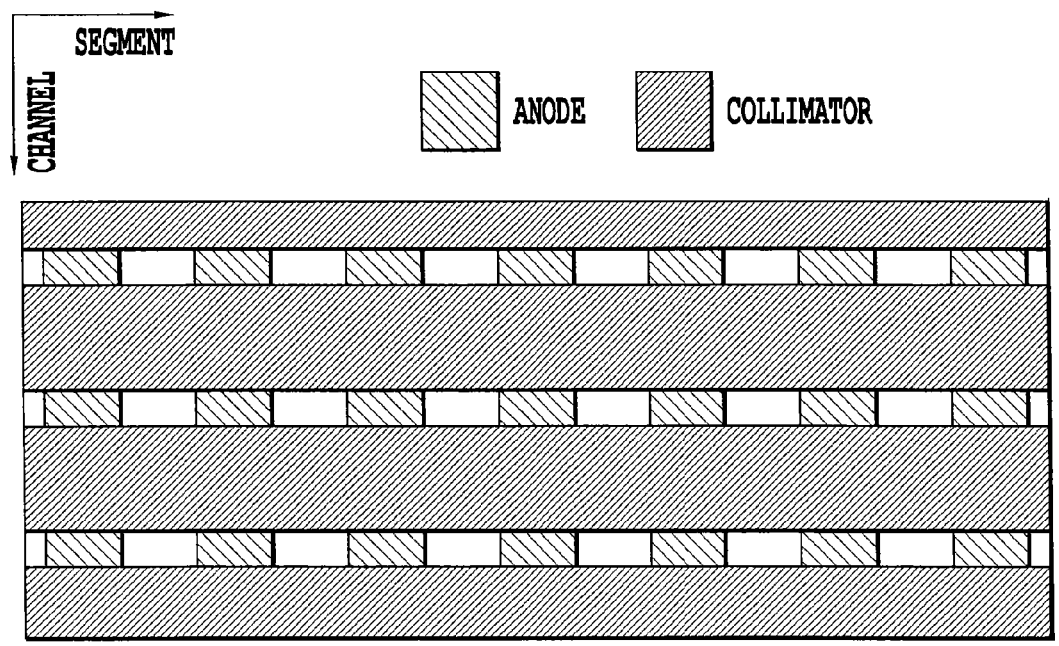

FIG. 7 illustrates another embodiment of a collimator pattern that includes collimator segments between each pixel in the channel direction. The collimator pattern illustrated in FIG. 7 is used when only inter-channel cross talk is a major concern.

As an example, it is sometimes useful to tilt the detectors in one direction to improve the energy resolution and count rate capability of the detectors. In this scenario, to cover the same area of an X-ray beam, a much larger area of the detector sensor is needed. The larger-area sensor is often read out by multiple anodes (pixels) and multiple electronics channels, but the signals will later be combined to form one signal. Crosstalk in this direction is not an issue.

Figure 8:
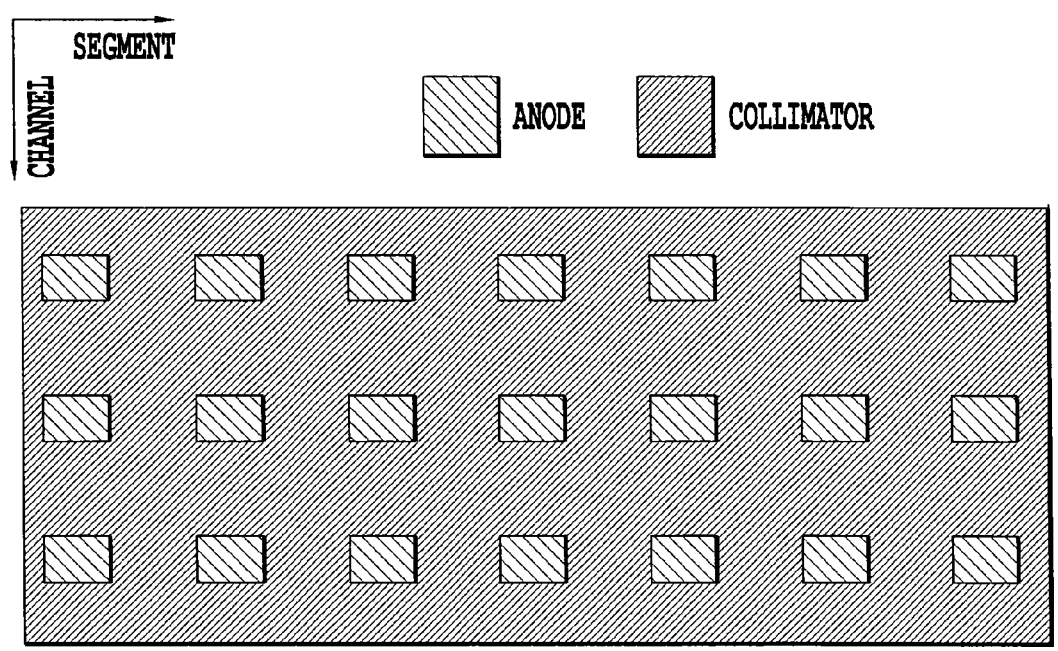

FIG. 8 illustrates another example collimator pattern that is used when both intersegment and inter-channel cross-talk are of major concern, and/or polarization is very severe. As illustrated in FIG. 8, the center of each pixel, i.e., anode, is left open while the rest of the PCD surface is blocked out by the collimator from receiving incident X-rays. As an example, severe polarization occurs when the incident flux is intrinsically high (high tube kVp, high tube mV, sub-optimal tube filter). Crosstalk occurs in both the segment and channel directions when the whole 2-D detector area is irradiated by X-ray photons and a signal is read out from each individual pixel, i.e., then there is no combining of pixel signals.

Figure 9A:
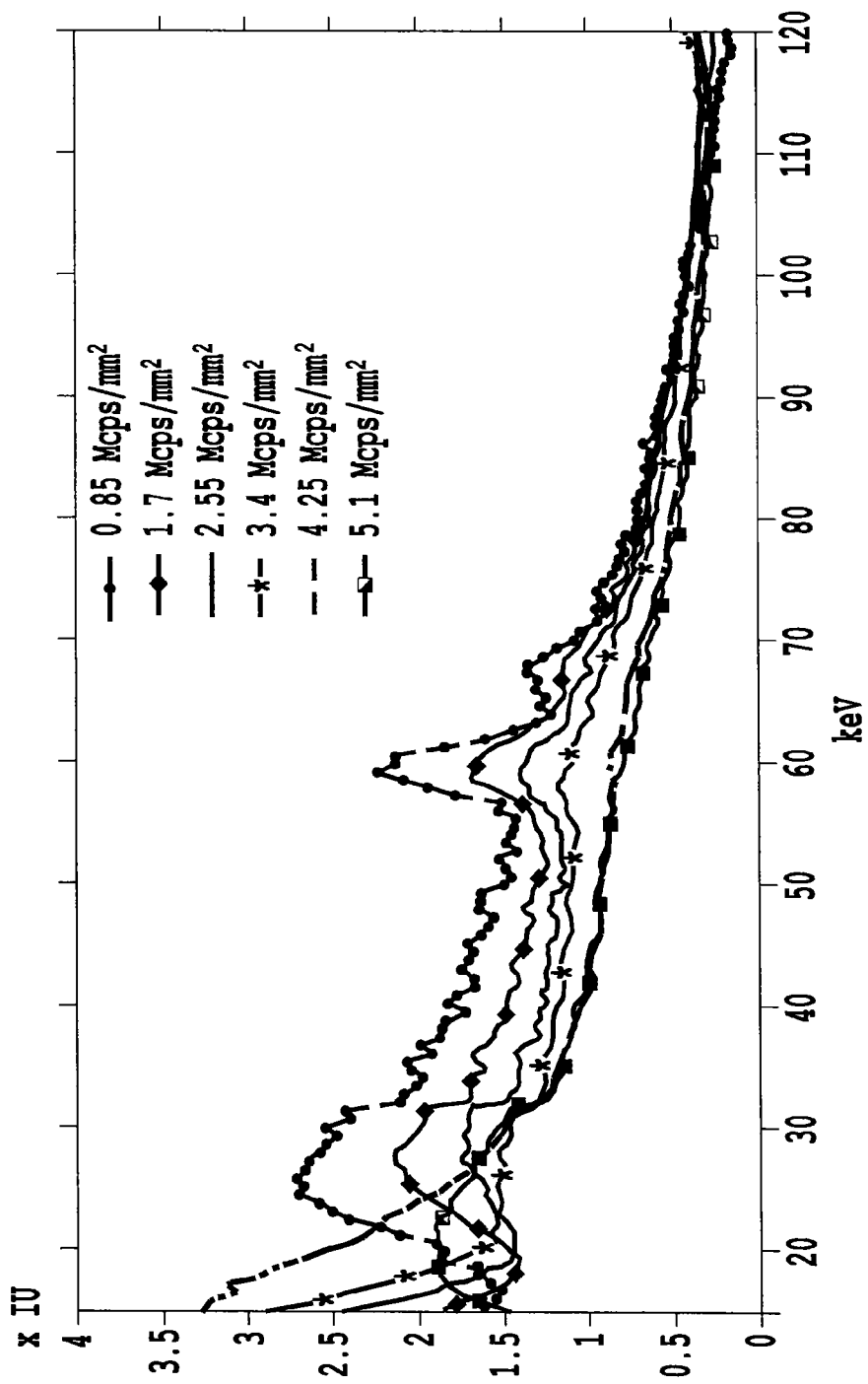
FIGS. 9A to 9D illustrate charts of obtained count rates of a PCD without a collimator and a PCD with a collimator.

FIG. 9A is a graph of count rates vs. X-ray photon energies at various counts per second per area with a PCD that uses no collimator. FIG. 9A shows typical signs of polarization and deteriorating spectral response at higher count rates. In this regard, as illustrated in FIG. 9C in the portion of the chart highlighted by box 900, there is crosstalk induced spectral distortion between the pixels (i.e., inter-pixel crosstalk).

Figure 9B:
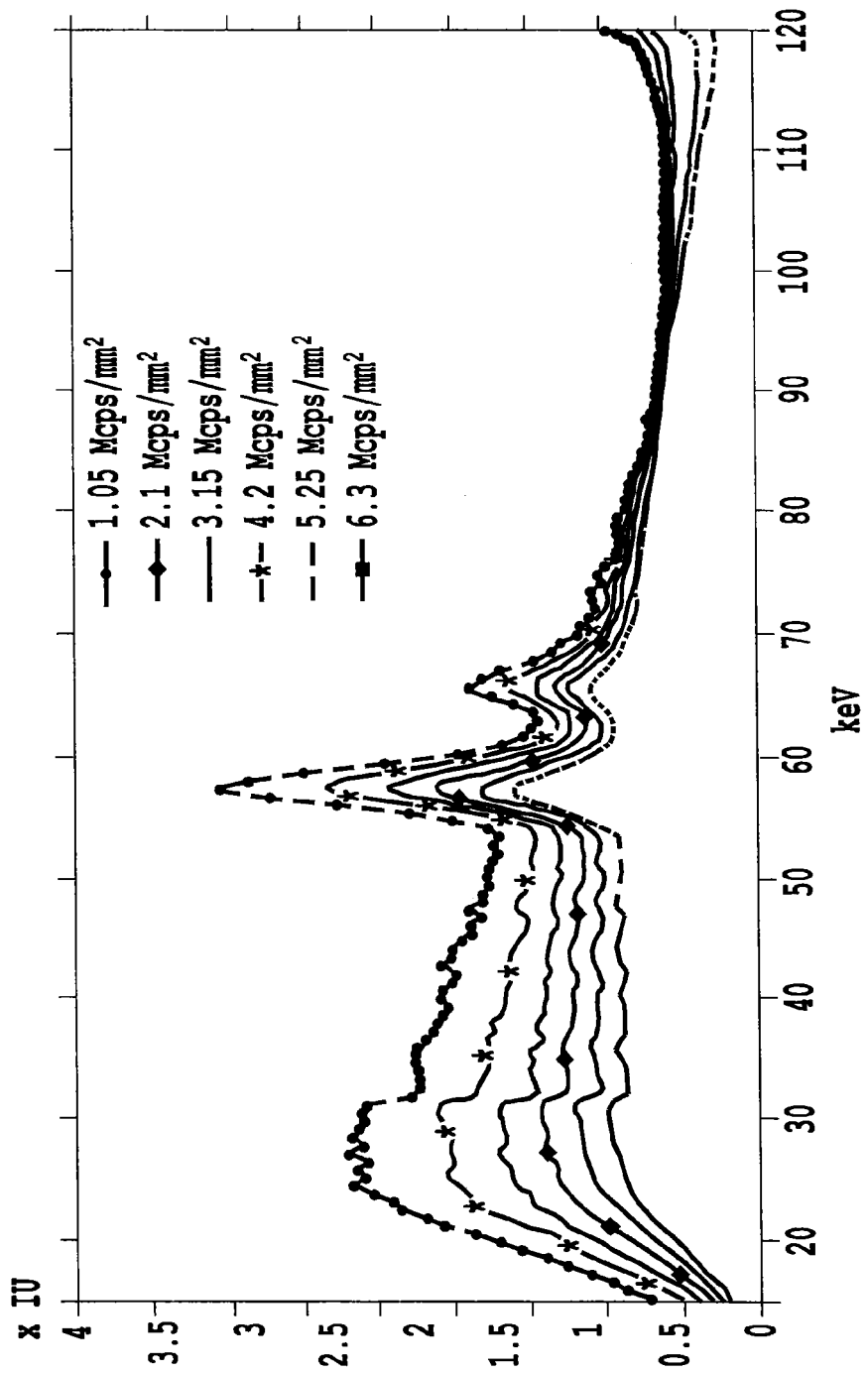
Figure 9C:
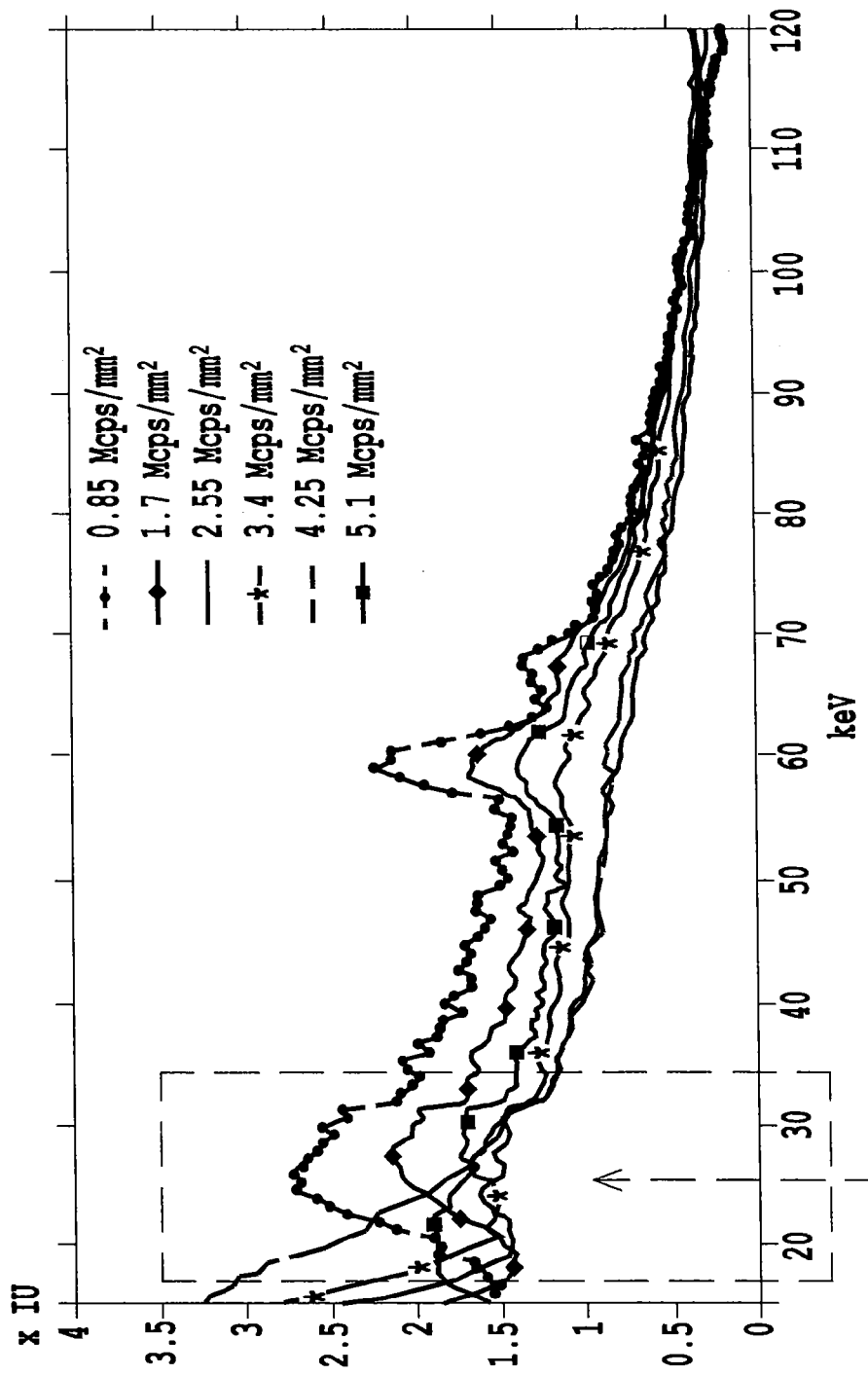
Figure 9D:
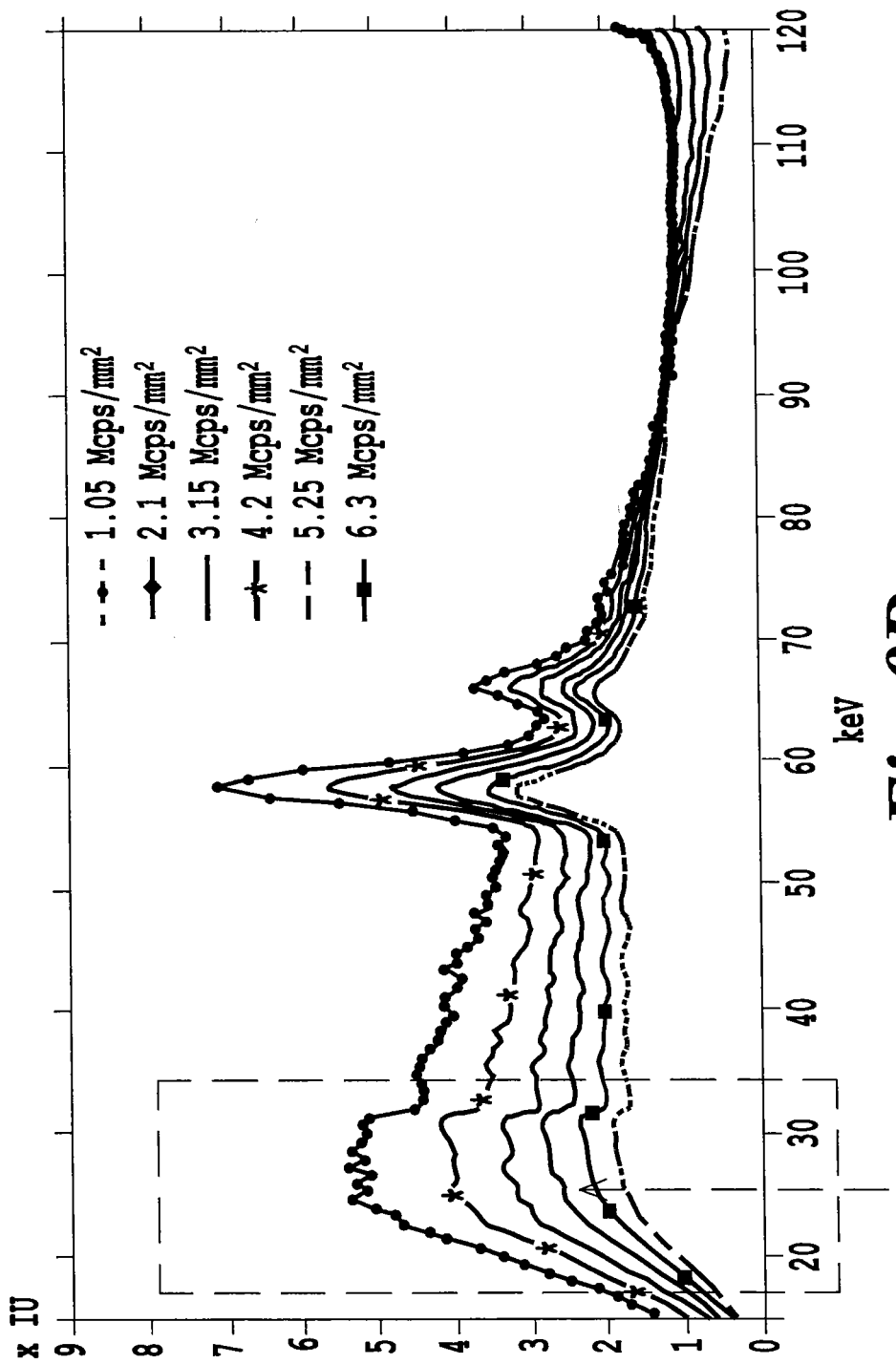

FIG. 9B illustrates a chart of count rates vs. X-ray photon energies at various counts per second per area for a PCD at various energies using a collimator. As an example, the chart illustrated in FIG. 9B is for a photon-counting detector using a collimator that provides 36% beam-size reduction. As illustrated in FIG. 9D, by using the collimator, there is significantly reduced distortion (902). In addition, the low-energy tailing observed in the X-ray spectra, mainly due to the inter-pixel cross-talk effect, can be reduced with the use of the collimators discussed herein.

Note that even with a 20% higher counts/·mm², the spectral response is restored. Further, the changing of spectra with increasing count rates is due to electronics pulse pileup, as understood by one of ordinary skill in the art. According to some embodiments, each of the charts illustrated in FIGS. 9A-9D are measured from the same detector channel on a pixellated CdZnTe detector (120-kVp, normalized by incident count rate).

Figure 10A:
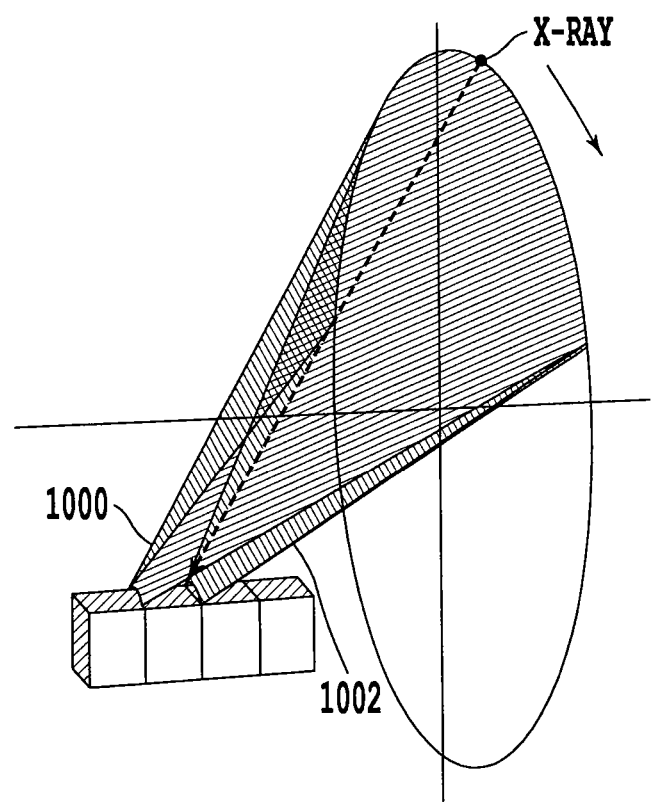
FIGS. 10A and 10B illustrate a sparse detector with collimators approximating a cone surface.

FIG. 10A illustrates a rotating X-ray source and a sparse and stationary 1-D PCD array including pixels P1 to P4. The arrow from the rotating X-ray source to the pixels P1 to P4 illustrates a primary beam in a detector fan in a multi-slice volume scan. As illustrated in FIG. 10A, two curved surfaces (1000, 1002) are defined by the primary beams and a detector fan for the pixel. According to some embodiments, curved collimators are defined by the two curved surfaces for a pixel. In one embodiment, a curved surface is placed on the boundary between every pair of adjacent pixels. For example, in a detector array including three pixels, a first curved surface is placed between the first and second pixel, and a second curved surface collimator is placed between the second and third pixel.

In one embodiment, collimators can be built for every pixel. In another embodiment, the heights of the collimators are determined by the dimensions of the detector and the scattered-primary ratio. The thickness of the collimators helps reduce the beam size for every pixel. As an example, the "thickness" of a collimator is mainly used to reduce (or eliminate) inter-pixel cross talk and increase the max flux level. According to one embodiment, the thickness of a collimator is dependent on the sensor pixel size and pitch. For example, one of ordinary skill in the art can experimentally decide the minimal thickness required to reduce the inter-pixel effects to an acceptable level. In additional embodiments, the thickness of a collimator is further dependent on the flux level for certain imaging tasks and the max flux/pixel that the detector can perform optimally. For example, one of ordinary skill in the art can experimentally decide the max gap between the Anti-scattering grid (ASG) (i.e., the minimal thickness) based on the intended imaging tasks and the actual detector performance.

Curved collimators in the Z (segment) direction allow primary beams across the detector fan to be collected, while rejecting scattered X-rays from the multi-slice imaging volume. According to some embodiments, the curved collimators are made of materials that do not emit K X-rays in the spectral range of interest, such as Mo. As an example, when X-rays interact with matter, the X-rays have a certain probability to undergo a photoelectric absorption (i.e., knocking out an inner-shell electron), which emits a secondary X-ray. The energy of this secondary X-ray is characteristic to the absorbing matter. If the secondary X-ray falls into the range of diagnostic X-rays, the secondary X-ray can be detected by the detector to create "fake" signals (not a result of object attenuation, as desired). The most significant secondary X-rays result from knocking out a K-shell electron, which is referred to as a K X-ray.

Figure 10B:
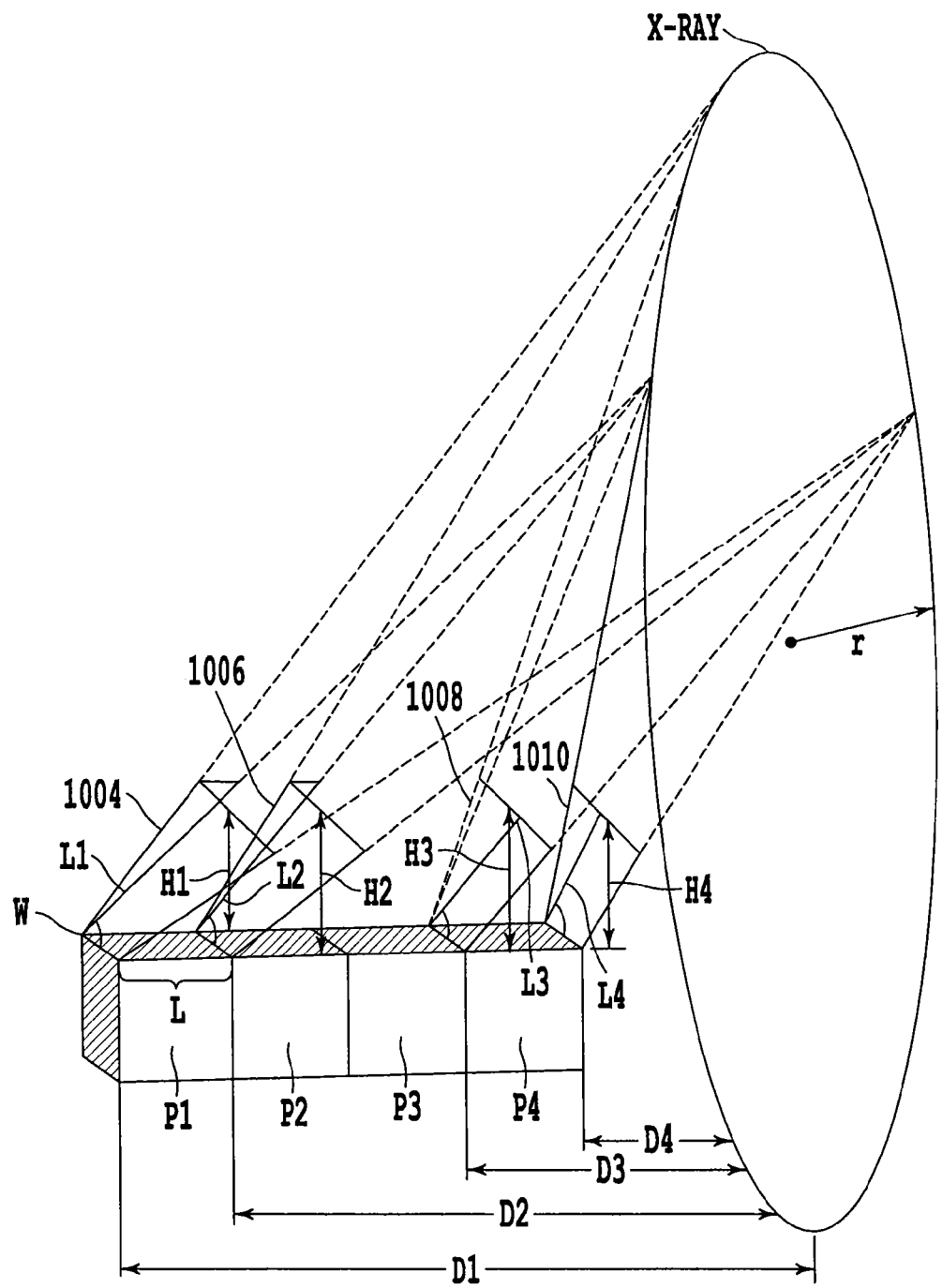

FIG. 10B illustrates curved collimators 1004, 1006, 1008, and 1010 between pixels P1 to P4. For illustration purposes only, no collimator is placed between pixels P2 and P3. However, in most embodiments collimators are included between every adjacent pixel. As illustrated in FIG. 10B, the curved anti-scattering collimators are a cutout from a cone-shaped surface. In particular, the base of the collimator corresponds to the width W of the pixel. As illustrated in FIG. 10B, each collimator can be a different height (H1-H4) and is angled at a different angle with respect to X-ray source trajectory. According to some embodiments, the heights of the respective collimators are 10 to 30 times the width of each detector pixel. In further embodiments, the length of each collimator (L1-L4) is determined by the desired primary-to-scatter ratio. As an example, the length of each collimator is empirically determined until the desired trade-off between scattering and image noise is achieved. As an example, the length is empirically optimized by simulation and/or actual measurements, where the length that gives a satisfactory figure of merit (i.e., image noise, contrast-to-noise ratio, primary-to-scatter ratio, etc.) is chosen. Furthermore, the angle of each collimator is determined in accordance with geometry. For example, the angles $\theta_1$-$\theta_4$ are determined in accordance with the distances (D1 to D4) of the pixels from the X-ray source plane, the distances of the pixels from the iso-center, and a radius R of the X-ray source plane. According to some embodiments, the curved collimators are created using a parametric design tool (e.g., Creo Elements, 3-D printers, etc.). By using curved collimators, when the X-ray source rotates, the stationary PCDs see the X-ray irradiation in a cone. Therefore, the curved collimators restrict the incident angle of the X-ray such that only direct radiation hits the detectors.

Figure 10C:
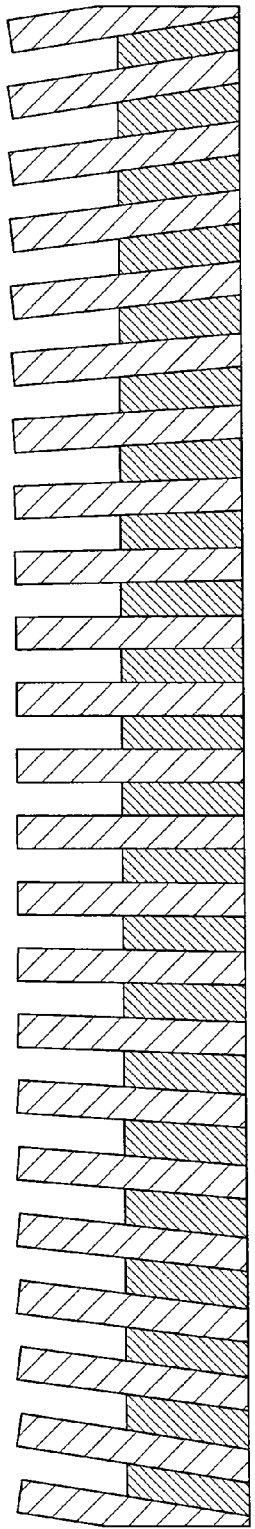
FIG. 10C illustrates an exemplary embodiment of an angled flat collimator.
Figure 11:
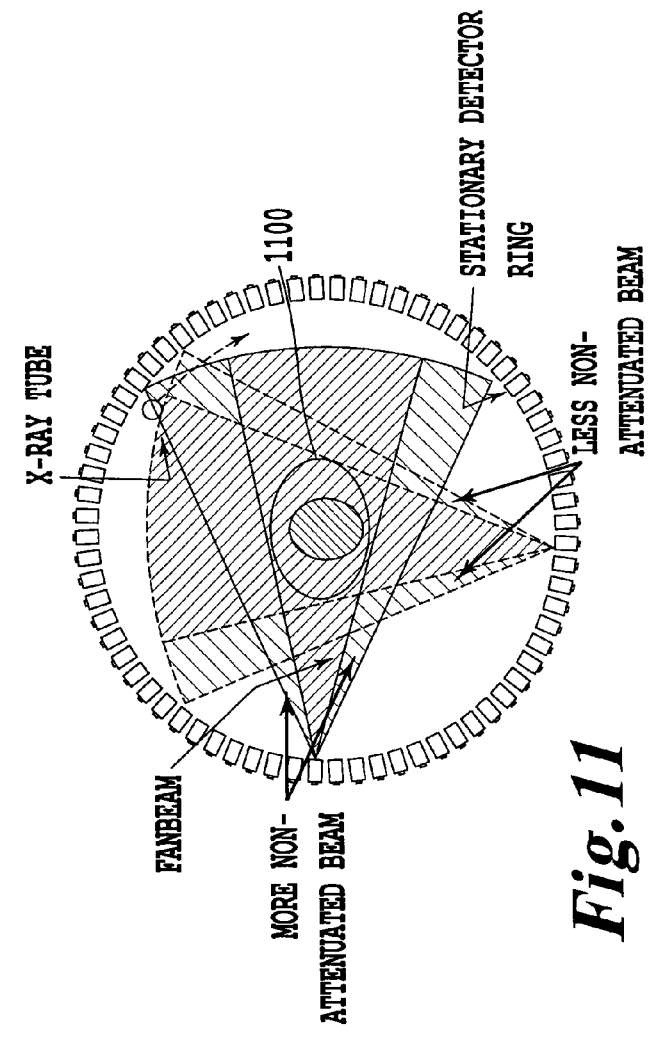
FIG. 11 illustrates a sparse X-ray ring detector with different levels of attenuation.

In an additional embodiment, FIG. 10C illustrates an embodiment including angled flat collimators. These angled flat collimators are focused toward the X-ray source and may be used in the Z (segment) direction to reject scattering and at the same time allow polar angle measurements on the sparse 4th-gen PCDs. As an example, the collimators illustrated in FIG. 10C are positioned in the same manner as the curved collimators 1004-1010 illustrated in FIG. 10B. In this regard, the angled flat collimator provide anti-scattering like the curved collimators 1004-1010. The collimators illustrated in FIGS. 5-8 may be used in conjunction with the angled flat collimators illustrated in FIG. 10C. In a further embodiment, FIG. 11 illustrates a stationary sparse detector ring along with a rotating X-ray tube. At the center of the X-ray field of view is an object 1100, which can represent a patient. As illustrated in FIG. 11, the fan beam of the X-ray tube can be attenuated at the edges of the object 1100. Accordingly, to attenuate the fan beam of the X-ray tube, additional collimation can be implemented in the XY plane. According to some embodiments, while a third-generation tube-side wedge assumes an axially symmetric object, the detector-side collimator for sparse, fourth-generation PCDs can work like a wedge to compensate for beam intensity at different tube angle positions, including the non-circular (e.g., elliptical) shape of the object. In some embodiments, the collimator is adjustable in the XY plane.

Figure 12A:
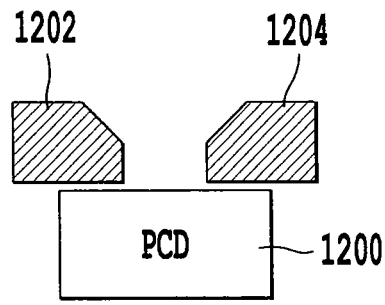
FIGS. 12A and 12B illustrate exemplary embodiments of wedge shaped collimators.
Figure 12B:
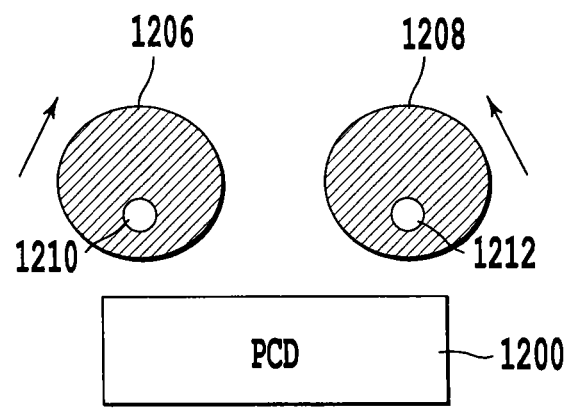

FIG. 12A illustrates one embodiment of a PCD 1200 that has wedge-shaped collimators 1202 and 1204 arranged in the XY plane. According to some embodiments, the shape of each collimator (i.e., adjustable opening) is optimized for every PCD based on the PCD's angular position in the scanner and the size of the patient. The collimators 1202 and 1204 have an inner height D and an opening width $O_W$ (i.e., opening distance) that is adjustable. See FIG. 14C. The value of $O_W$ is dependent on the angular position of the PCD with respect to a patient. FIG. 12B illustrates another embodiment of PCD 1200 with adjustable collimators 1206 and 1208 in the XY plane. According to some embodiments, collimators 1206 and 1208 are adjusted by rotating around the illustrated pivot points 1210 and 1212, respectively, to provide a varying effective opening for the PCD.

Figure 13B:
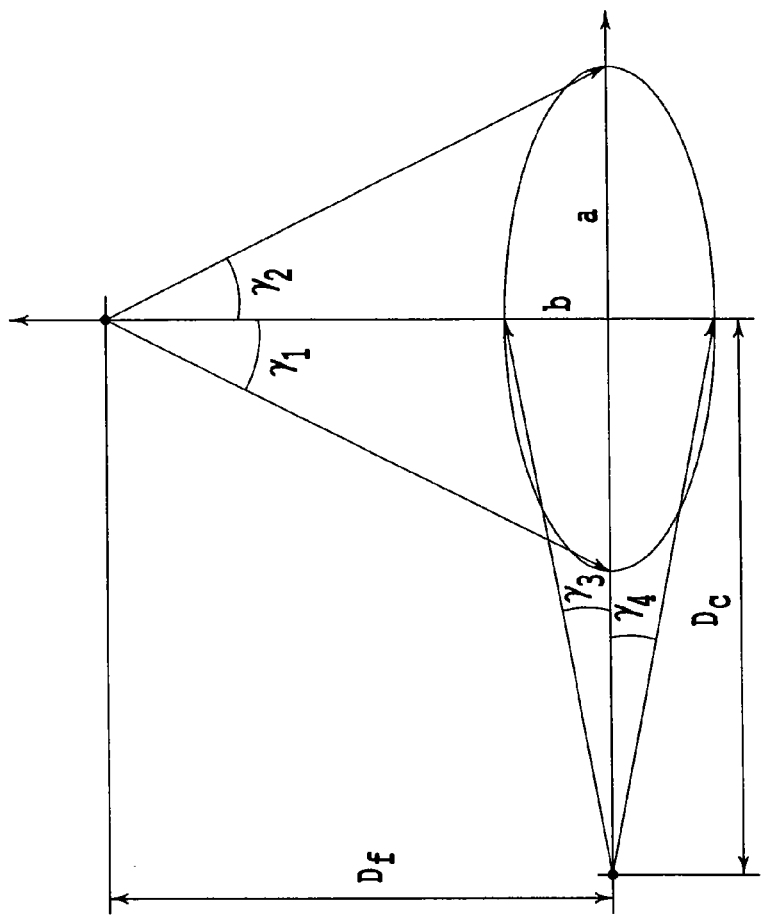
FIG. 13B illustrates an exemplary embodiment of a two-dimensional scanogram.
Figure 13A:
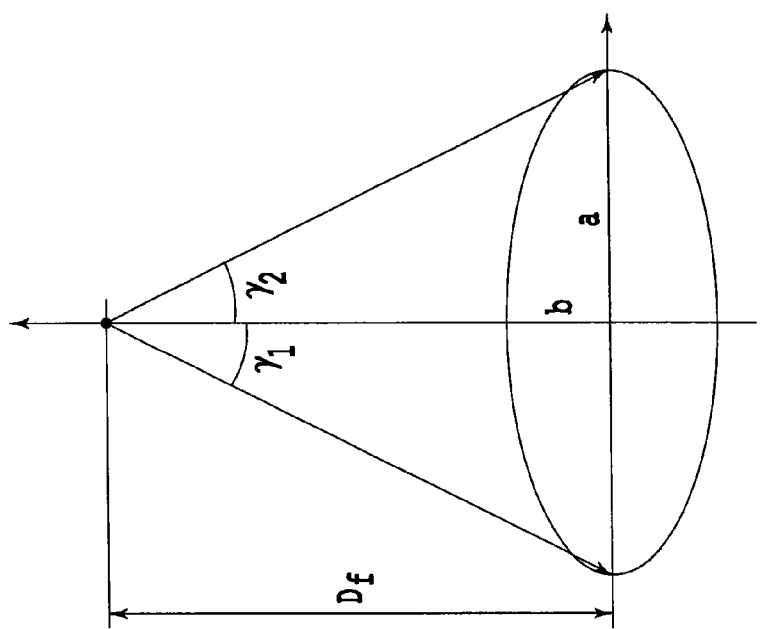
FIG. 13A illustrates an exemplary embodiment of a one-dimensional scanogram.

FIG. 13A illustrates an embodiment of a one-view scanogram of a patient. The subject is represented as an ellipse having axises of length "a" and "b." The scanogram is used to find rays passing the edges of the subject. As an example, given a generated scanogram, the identification of the rays passing the edges may be performed by either manual identification (an operator drawing out a region-of-interest containing the edge), or computerized image processing methods (edge detection, pixel value thresholding, etc.). After the rays passing the edges of the subject are determined, the parameters $\gamma_1$ and $\gamma_2$ are determined.

In one embodiment, axis lengths "a" and "b" are determined by the following equations:

$$a = D_f^*(\tan \gamma_1 + \tan \gamma_2)/2$$

$$b = 0.5 * p_c/\mu(\text{water}),$$

where $D_f$ represents the focal-isocenter-distance, $p_c$ is the ray sum passing the center of the subject, and $\mu(\text{water})$ is the average linear attenuation coefficient of water. As an example, the ray sum is the line integral of the average linear attenuation coefficient along a certain path (e.g., in this case, along the short axis b). A scanogram image provides the ray sum values along the X-ray source and the detector pixel which receives the incident X-rays from the X-ray source.

FIG. 13B illustrates an embodiment for a two-view scanogram. In some embodiments, the two-view scanogram includes scans from two views separated by 90°. As with the one-view scanogram, the two-view scanogram is used to find the rays passing the edges of the subject. In one embodiment, using the two-view scanogram, axis lengths "a" and b" are determined as follows:

$$a = D_f^*(\tan \gamma_1 + \tan \gamma_2)/2$$

$$b = D_f^*(\tan \gamma_3 + \tan \gamma_4)/2$$

FIG. 14A illustrates a positioning of a PCD with adjustable wedge collimators at an angle θ with respect to a center of the subject. The axis lengths "a" and "b" are obtained using either the one-view or two-view scanograms, as discussed above. According to some embodiments, the angles $\phi_1$ and $\phi_2$ are the two solutions of the following equations, where $D_{pcd}$ is the distance from the PCD to the isocenter:

$$\left(\frac{1}{a}\cos(\theta+\varphi)\right)^2 + \left(\frac{1}{b}\sin(\theta+\varphi)\right)^2 = \left(\frac{D_{pcd}}{ab}\right)^2 \sin^2(\varphi)$$

The above equation is a quadratic equation that produces one non-negative (positive or zero) and one non-positive (negative or zero) solution. In one embodiment, referring to FIG. 14A, $\phi_1$ is the non-positive solution and $\phi_2$ is the non-negative solution.

FIG. 14B illustrates a view of the opening width $O_W$ without the wedge shaped collimators. FIG. 14C illustrates an expanded view of the opening width $O_w$. According to some embodiments, the opening width $O_w$ is determined in accordance with the following equation:

$$O_w = d^*(\tan \phi_1 + \tan \phi_2)$$

With respect to the collimators illustrated in FIG. 12B, in some embodiments, the value of "d" corresponds to the diameter of the circular collimators 1206 and 1208. As an example, based on the diameter d of the circular collimators, and the angles $\phi_1$ and $\phi_2$, the value $O_w$ is obtained where the collimators are rotated around the pivot point until the desired distance ($O_w$) between the collimators is obtained.

Figure 15:
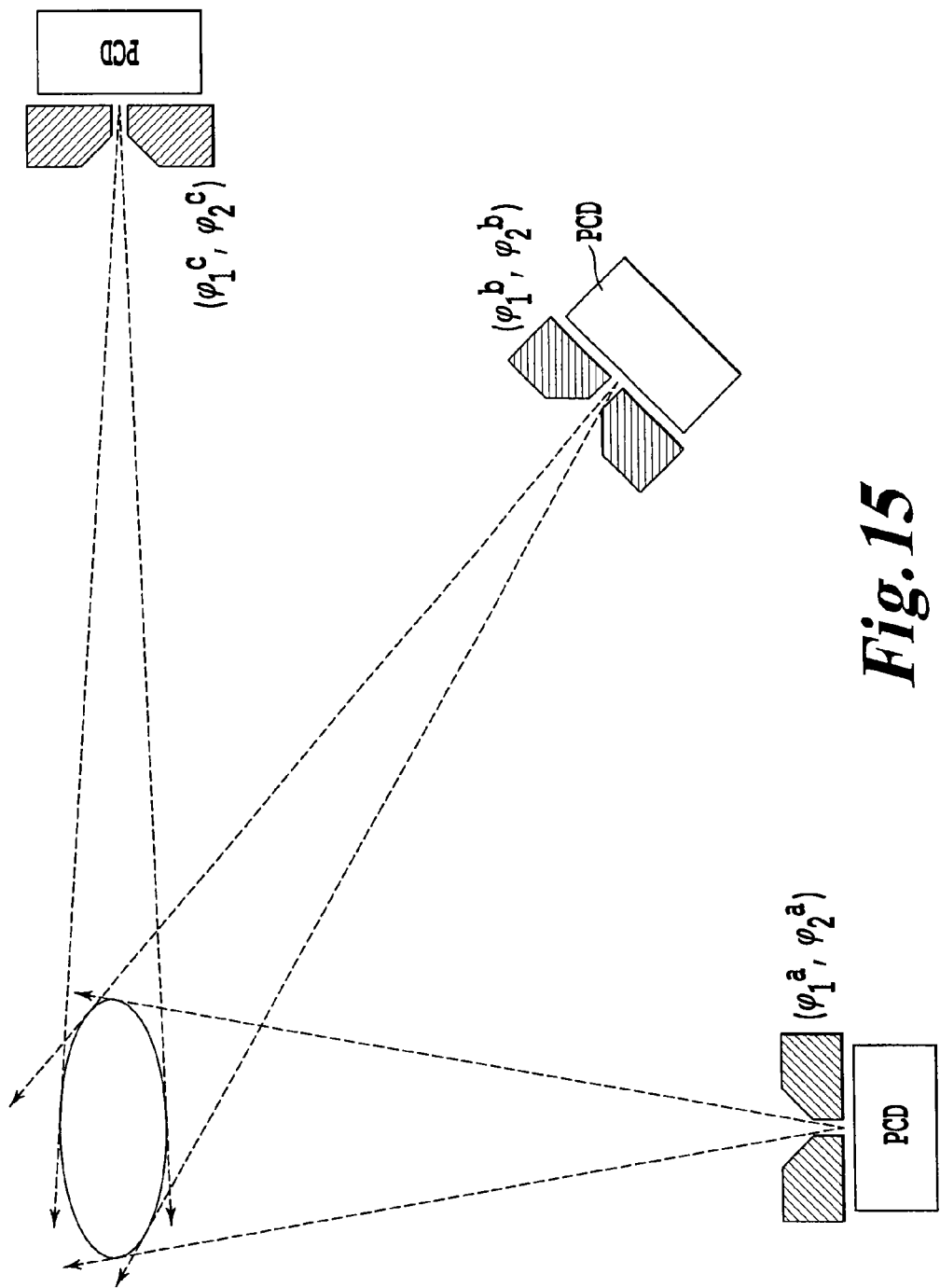
FIG. 15 illustrates a configuration of a plurality of PCDs with adjustable wedge-shaped collimators.

FIG. 15 illustrates a configuration of PCDs 1500, 1502, and 1504 with respect to a center object. As illustrated in FIG. 15, each of the PCDs has different different θ angles with respect to the object, and therefore, would have different corresponding opening widths.

Figure 16:
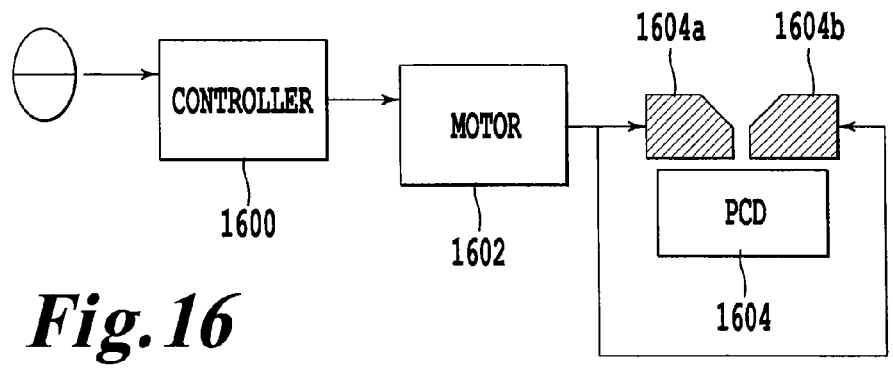
FIG. 16 illustrates an exemplary embodiment of a controller for adjusting an opening of wedge-shaped collimators.

FIG. 16 illustrates an embodiment of a controlling apparatus for adjusting the opening width of wedge collimators. As illustrated in FIG. 16, the θ angle between a PCD 1604 and an object is input into the controller 1600. The controller 1600 subsequently uses the θ angle to determine the angles $\phi_1$ and $\phi_2$ in accordance with the embodiments described above. The controller subsequently determines an opening width ($O_w$) for the wedge collimators on the PCD 1604 using the method described above. Upon determining the opening width, the controller 1600 determines an appropriate adjustment value which is sent to the motor 1602. As an example, the adjustment value is the difference between the determined opening width and a current opening width of the pair of wedge collimators. Based on the adjustment value, the motor 1602 moves wedge collimators 1604A and 1604B to obtain the appropriate determined opening width.

Although FIG. 16 illustrates only one PCD and one motor, further embodiments include a motor for each PCD in the detection ring, wherein the controller is connected to each motor and PCD in the detector ring. In alternative embodiments, each PCD in an X-ray detector ring includes an individual controller and motor. Furthermore, motor 1602 can be any motor known to one of ordinary skill in the art, such as a stepping motor or pulse-width-modulation motor.

Figure 17:
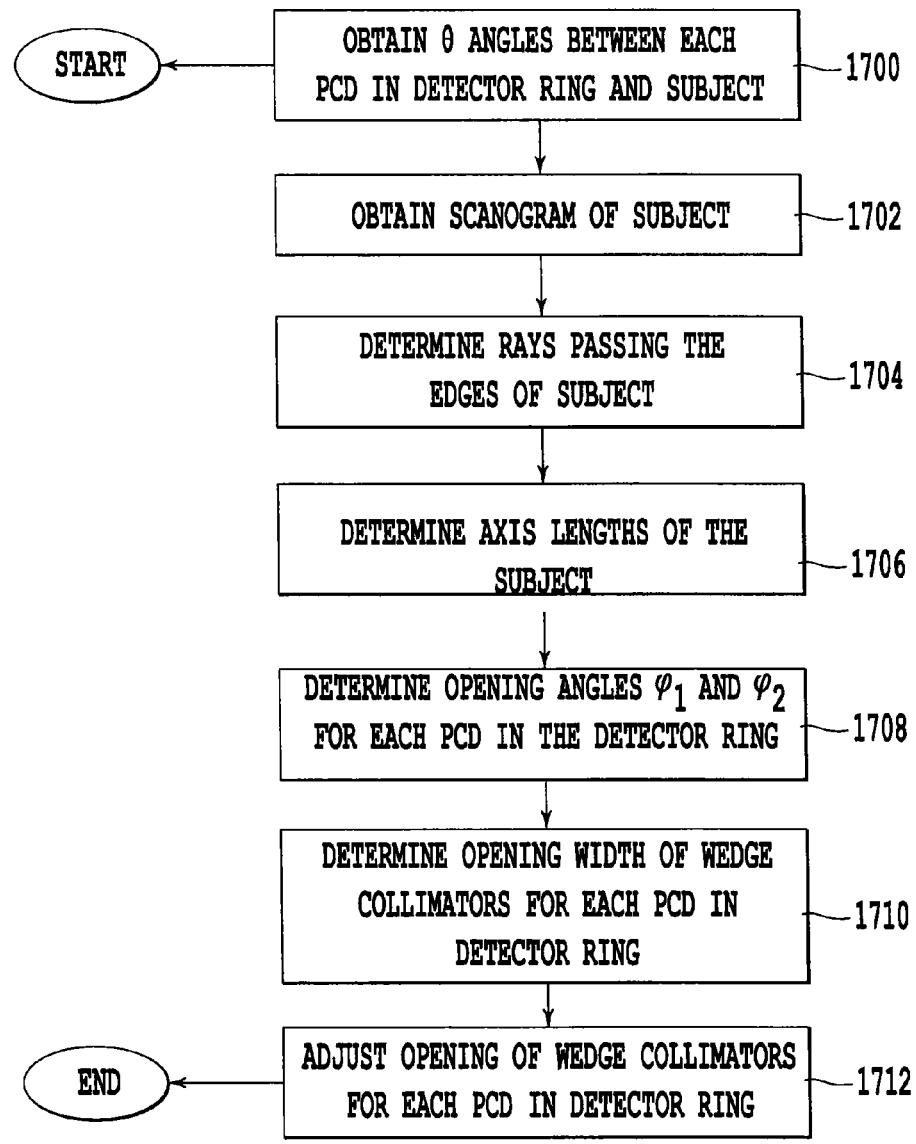
FIG. 17 illustrates an exemplary process for adjusting an opening of wedge-shaped collimator.

FIG. 17 illustrates an embodiment of a process for determining an opening width between wedge collimators positioned over a PCD. In some embodiments, the process starts at step 1700 to obtain the θ angles for each PCD in an X-ray detector ring. These θ angles may be predetermined measured values that are stored in memory and retrieved by controller 1600 (FIG. 16).

The process proceeds to step 1702 to obtain a scanogram of a subject or patient. As an example, a one-view scanogram or two-view scanogram can be obtained as described above.

In step 1704, the rays passing the edges of the subject are determined.

In step 1706, the axis lengths "a" and "b" of the subject are determined. For example, the axis lengths "a" and "b" are determined based on whether a one view scanogram or two view scanogram is used in accordance with embodiments described above.

In step 1708, the angles $\phi_1$ and $\phi_2$ are determined for each PCD in the X-ray detector ring in accordance with the embodiments described above.

In step 1710, the opening of the wedge collimator is determined in accordance with the embodiments described above.

In step 1712, the opening of the wedge collimator is adjusted for each PCD in the X-ray detector ring. For example, the current opening width for each PCD in the X-ray detector ring is obtained. An adjustment value for each PCD in the X-ray detector ring is determined based on the difference between a respective opening width determined in step 1710 and a respective current opening width. The process illustrated in FIG. 17 ends, according to some embodiments, after the opening of the wedge collimator is adjusted. In additional embodiments, any desired measuring system can be used to make additional corrections to the wedge collimator after the wedge collimators are adjusted.

Figure 18:
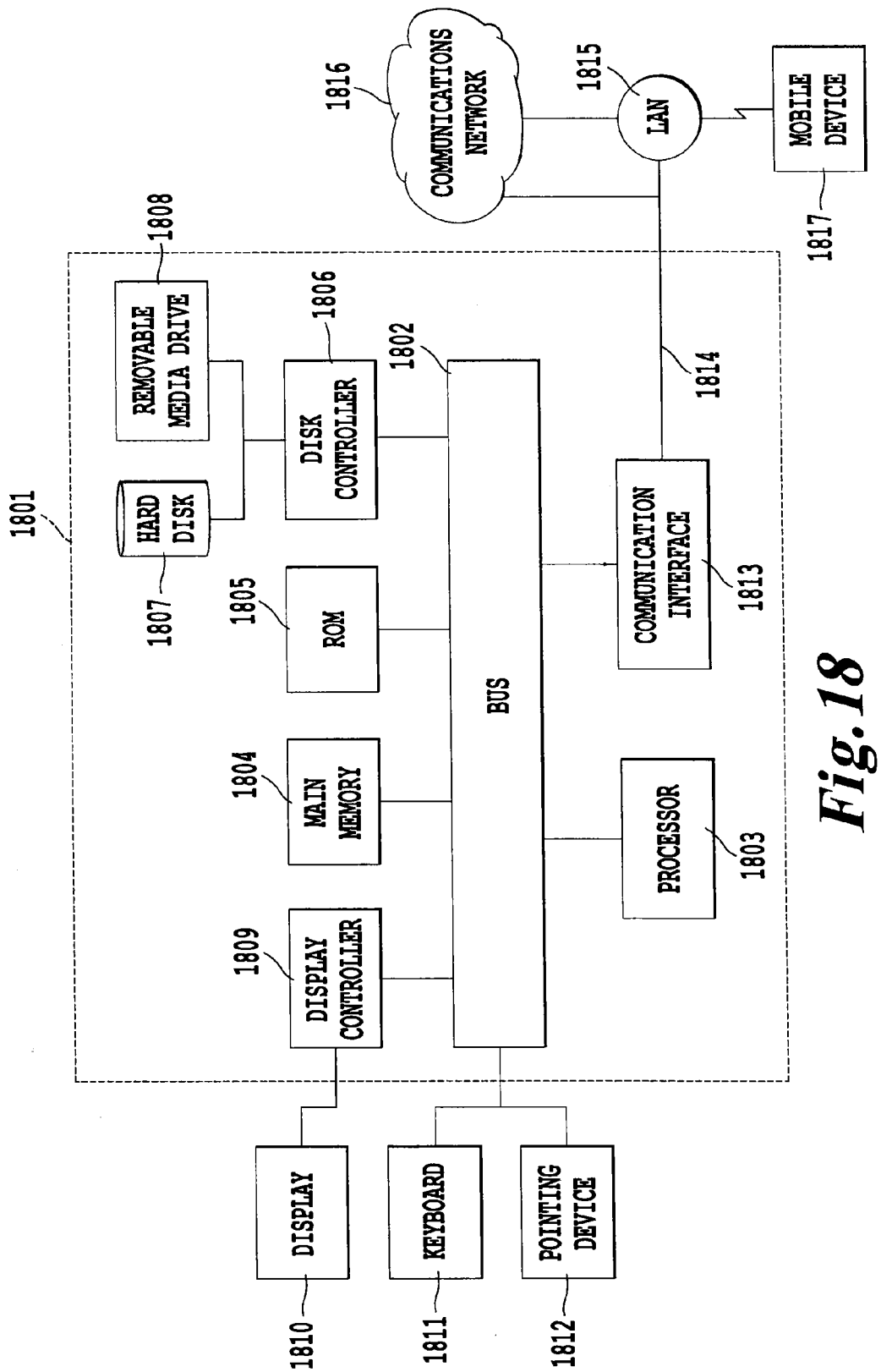
FIG. 18 illustrates an exemplary embodiment of a processor.

FIG. 18 illustrates a computer system 1801 that functions as, for example, the processor 106 (FIG. 1) or the controller 1600 (FIG. 16). The computer system 1801 may be used to perform any method described herein such as the method illustrated in FIG. 17.

The computer system 1801 includes a disk controller 1806 coupled to the bus 1802 to control one or more storage devices for storing information and instructions, such as a magnetic hard disk 1807, and a removable media drive 1808 (e.g., floppy disk drive, read-only compact disc drive, read/write compact disc drive, compact disc jukebox, tape drive, and removable magneto-optical drive). The storage devices may be added to the computer system 1801 using an appropriate device interface (e.g., small computer system interface (SCSI), integrated device electronics (IDE), enhanced-IDE (E-IDE), direct memory access (DMA), or ultra-DMA).

The computer system 1801 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1801 may also include a display controller 1809 coupled to the bus 1802 to control a display 1810, for displaying information to a computer user. The computer system includes input devices, such as a keyboard 1811 and a pointing device 1812, for interacting with a computer user and providing information to the processor 1803. The pointing device 1818, for example, may be a mouse, a trackball, a finger for a touch screen sensor, or a pointing stick for communicating direction information and command selections to the processor 1803 and for controlling cursor movement on the display 1810.

The processor 1803 executes one or more sequences of one or more instructions contained in a memory, such as the main memory 1804. Such instructions may be read into the main memory 1804 from another computer readable medium, such as a hard disk 1807 or a removable media drive 1808. One or more processors in a multi-processing arrangement may also be employed to execute the sequences of instructions contained in main memory 1804. In alternative embodiments, hard-wired circuitry may be used in place of or in combination with software instructions. Thus, embodiments are not limited to any specific combination of hardware circuitry and software.

As stated above, the computer system 1801 includes at least one computer readable medium or memory for holding instructions programmed according to the teachings of the present disclosure and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes.

Stored on any one or on a combination of computer readable media, the present disclosure includes software for controlling the computer system 1801, for driving a device or devices for implementing the invention, and for enabling the computer system 1801 to interact with a human user. Such software may include, but is not limited to, device drivers, operating systems, and applications software. Such computer readable media further includes the computer program product of the present disclosure for performing all or a portion (if processing is distributed) of the processing performed in implementing the invention.

The computer code devices of the present embodiments may be any interpretable or executable code mechanism, including but not limited to scripts, interpretable programs, dynamic link libraries (DLLs), Java classes, and complete executable programs. Moreover, parts of the processing of the present embodiments may be distributed for better performance, reliability, and/or cost.

The term "computer readable medium" as used herein refers to any non-transitory medium that participates in providing instructions to the processor 1803 for execution. A computer readable medium may take many forms, including but not limited to, non-volatile media or volatile media. Non-volatile media includes, for example, optical, magnetic disks, and magneto-optical disks, such as the hard disk 1807 or the removable media drive 1808. Volatile media includes dynamic memory, such as the main memory 1804. Transmission media, on the contrary, includes coaxial cables, copper wire and fiber optics, including the wires that make up the bus 1802. Transmission media also may also take the form of acoustic or light waves, such as those generated during radio wave and infrared data communications.

Various forms of computer readable media may be involved in carrying out one or more sequences of one or more instructions to processor 1803 for execution. For example, the instructions may initially be carried on a magnetic disk of a remote computer. The remote computer can load the instructions for implementing all or a portion of the present disclosure remotely into a dynamic memory and send the instructions over a telephone line using a modem. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art.

A modem local to the computer system 1801 may receive the data on the telephone line and place the data on the bus 1802. The bus 1802 carries the data to the main memory 1804, from which the processor 1803 retrieves and executes the instructions. The instructions received by the main memory 1804 may optionally be stored on storage device 1807 or 1808 either before or after execution by processor 1803.

As one of ordinary skill in the art would recognize, the processor 1803 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. The processor 1803 may execute a computer program including a set of computer-readable instructions that perform the functions described herein, the program being stored in any of the above-described non-transitory electronic memories and/or a hard disk drive, CD, DVD, FLASH drive or any other known storage media. Once processed by the CPU, the processed signals are passed to a reconstruction processor, which is configured to generate CT images. The images are stored in the memory, and/or displayed on a display.

The computer system 1801 also includes a communication interface 1813 coupled to the bus 1802. The communication interface 1813 provides a two-way data communication coupling to a network link 1814 that is connected to, for example, a local area network (LAN) 1815, or to another communications network 1816 such as the Internet. For example, the communication interface 1813 may be a network interface card to attach to any packet switched LAN. As another example, the communication interface 1813 may be an integrated services digital network (ISDN) card. Wireless links may also be implemented. In any such implementation, the communication interface 1813 sends and receives electrical, electromagnetic or optical signals that carry digital data streams representing various types of information.

The network link 1814 typically provides data communication through one or more networks to other data devices. For example, the network link 1814 may provide a connection to another computer through a local network 1815 (e.g., a LAN) or through equipment operated by a service provider, which provides communication services through a communications network 1816. The local network 1814 and the communications network 1816 use, for example, electrical, electromagnetic, or optical signals that carry digital data streams, and the associated physical layer (e.g., CAT 5 cable, coaxial cable, optical fiber, etc.). The signals through the various networks and the signals on the network link 1814 and through the communication interface 1813, which carry the digital data to and from the computer system 1801, may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1801 can transmit and receive data, including program code, through the network(s) 1815 and 1816, the network link 1814 and the communication interface 1813. Moreover, the network link 1814 may provide a connection through a LAN 1815 to a mobile device 1817 such as a personal digital assistant (PDA) laptop computer, or cellular telephone.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A computed-tomography (CT) apparatus, comprising:
a CT scanner including a rotating X-ray source;
a photon-counting detector (PCD) array including a plurality of PCDs, each PCD configured to capture incident X-ray photons emitted from the X-ray source; and
a collimator arranged on one of the PCDs in the PCD array and having a curved surface extending away from an edge of the one of the PCDs towards the X-ray source to block a portion of X-ray photons emitted from the X-ray source.

2. The CT apparatus according to claim 1, wherein the PCD array is sparse and stationary.

3. The CT apparatus according to claim 1, wherein the collimator has a height proportional to a width of the one of the PCDs included in the PCD array.

4. The CT apparatus according to claim 1, wherein the curved surface of the collimator is determined according to a width of the one of the PCDs and a distance of the one of the PCDs from the X-ray source.

5. A computed-tomography (CT) apparatus, comprising:
a CT scanner including a rotating X-ray source;
a plurality of photon-counting detectors (PCDs) arranged in a fixed detector ring around the X-ray source to capture incident X-ray photons emitted from the X-ray source; and
a pair of adjustable wedge-shaped collimators arranged on a surface of one of the PCDs to block X-ray photons emitted from the X-ray source.

6. The apparatus according to claim 5, further comprising:
a controller configured to determine an angle between a line from the one PCD to a center of an imaging subject centered in the fixed detector ring and an axis passing through the center of the imaging subject, and determine an opening distance between the pair of adjustable wedge-shaped collimators in accordance with the determined angle; and at least one motor configured move the pair of adjustable wedge-shaped collimators of the at least one PCD in accordance with the determined opening distance.

7. The apparatus according to claim 6, wherein the controller is configured to determine the opening distance in accordance with a height of an inner edge of the pair of adjustable wedge-shaped collimators and the determined angle.

8. The apparatus according to claim 7, wherein the controller is further configured to determine the opening distance in accordance with a size of the imaging subject, which is determined from a scanogram.

9. A method to determine an opening distance of a pair of adjustable wedge-shaped collimators positioned on a photon-counting detector (PCD), the method comprising:
performing a scanogram of an imaging subject centered with respect to a rotating X-ray source;
determining, using information from the scanogram, a pair of axis lengths of a pair of perpendicular axes that pass through a center of the imaging subject;
determining an angle between a line from the PCD to the center of the imaging subject and one of the axes from the pair of perpendicular axes;
determining the opening distance of the pair of adjustable wedge-shaped collimators using at least the determined pair of axis lengths and the determined angle; and
adjusting an opening between the pair of adjustable wedge-shaped collimators in accordance with the determined opening distance.

10. The method according to claim 9, wherein the step of determining the opening distance further comprises:
determining the opening distance in accordance with a height of an inner edge of the pair of adjustable wedge-shaped collimators.

11. The method according to claim 9, wherein when the scanogram is a one-view scanogram, a first axis length from the pair of axis lengths is determined using $$a=D_f*(\tan \gamma_1+\tan \gamma_2)/2,$$

wherein "a" is the first axis length of a first axis from the pair of axes, $D_f$ is a distance from the X-ray source to the center of the subject, $\gamma_1$ is an angle between the center of the subject and a first edge of the subject that intersects the first axis, and $\gamma_2$ is an angle between the center of the subject and a second edge of the subject that is a 180° from the first edge and intersects the first axis.

12. The method according claim 11, wherein when the scanogram is the one-view scanogram, a second axis length from the pair of axis lengths is determined using $$b=0.5*p_c/\mu(\text{water}),$$

wherein b is the second axis length of a second axis from the pair of axes that is perpendicular to the first axis, $p_c$ is a ray sum passing the center of the subject, and $\mu(\text{water})$ is the average linear attenuation coefficient of water.

13. The method according to claim 11, wherein when the scanogram is a two-view scanogram, a first axis length from the pair of axis lengths is determined using $$a=D_f*(\tan \gamma_1+\tan \gamma_2)/2,$$

wherein "a" is the first axis length of a first axis from the pair of axes, $D_f$ is a distance from the X-ray source to the center of the subject, $\gamma_1$ is an angle between the center of the subject and a first edge of the subject that intersects the first axis, and $\gamma_2$ is an angle between the center of the subject and a second edge of the subject that is a 180° from the first edge and intersects the first axis, and a second axis length from the pair of axis lengths is determined using $$b=D_f*(\tan \gamma_3+\tan \gamma_4)/2,$$

wherein b is the second axis length of a second axis from the pair of axes that is perpendicular to the first axis, $\gamma_3$ is an angle between the center of the subject and a third edge of the subject that intersects the second axis, and $\gamma_4$ is an angle between the center of the subject and a fourth edge of the subject that is a 180° from the third edge and intersects the second axis.

14. A computed-tomography (CT) apparatus, comprising:
a CT scanner including a rotating X-ray source;
a photon-counting detector (PCD) array including a plurality of stationary PCDs, each stationary PCD configured to capture incident X-ray photons emitted from the X-ray source; and
a collimator arranged on one of the stationary PCDs in the PCD array and having at least one flat surface extending away from an edge of the one of the stationary PCDs and being tilted in a direction of a longitudinal axis of a patient and toward a part of a trajectory of the X-ray source to block a portion of X-ray photons emitted from the X-ray source.

15. The CT apparatus of claim 1, wherein each PCD includes
a detector layer, the detector layer including a photon-counting semiconductor material;
a cathode layer arranged adjacent to the detector layer;
a plurality of pixelated anodes arranged adjacent to the detector layer on a side opposite to the cathode layer; and
a plurality of collimator segments arranged above the cathode layer so as to block a portion of X-ray photons emitted from an X-ray source from reaching the anodes, wherein
each collimator segment is arranged opposite a portion of at least one anode.

16. The CT apparatus of claim 15, wherein the detector layer is composed of bulk CdTe/CZT.

17. The CT apparatus of claim 15, wherein the collimator segments are arranged to cover between 10% to 60% of a surface area of the anodes.

18. The CT apparatus of claim 15, wherein
the plurality of pixelated anodes are arranged in a two-dimensional grid pattern having a plurality of columns and rows; and
the collimator segments are positioned to cover the detector layer between each column of pixelated anodes.

19. The CT apparatus of claim 15, wherein
the plurality of pixelated anodes are arranged in a two-dimensional grid pattern having a plurality of columns and rows; and
the collimator segments are positioned to cover the detector layer between every other column of pixelated anodes.

20. The CT apparatus of claim 15, wherein the collimator segments block the X-ray photons emitted from the X-ray source from reaching the anodes, except for a center portion of each pixelated anode.

21. The CT apparatus of claim 14, wherein the at least one flat surface has points, each of which covers different positions of the trajectory.

* * * * *